United States Patent
Takats

(10) Patent No.: US 9,805,922 B2
(45) Date of Patent: Oct. 31, 2017

(54) SYSTEM AND METHOD FOR RAPID EVAPORATIVE IONIZATION OF LIQUID PHASE SAMPLES

(71) Applicant: MICROMASS UK LIMITED, Wilmslow (GB)

(72) Inventor: Zoltan Takats, Budapest (HU)

(73) Assignee: MICROMASS UK LIMITED, Wilmslow (GB)

(*) Notice: Subject to any disclaimer, the term of this patent is extended or adjusted under 35 U.S.C. 154(b) by 0 days.

(21) Appl. No.: 15/050,254

(22) Filed: Feb. 22, 2016

(65) Prior Publication Data
US 2016/0240361 A1    Aug. 18, 2016

Related U.S. Application Data

(63) Continuation of application No. 14/368,796, filed as application No. PCT/IB2012/003009 on Dec. 28, 2012, now Pat. No. 9,281,174.
(Continued)

(51) Int. Cl.
*H01J 49/16* (2006.01)
*G01N 27/62* (2006.01)
(Continued)

(52) U.S. Cl.
CPC ............ *H01J 49/16* (2013.01); *A61B 5/20* (2013.01); *A61B 5/4845* (2013.01);
(Continued)

(58) Field of Classification Search
CPC .... H01J 49/16; H01J 49/0031; H01J 49/0431; A61B 5/20; A61B 5/4845; A61B 5/4866;
(Continued)

(56) References Cited

U.S. PATENT DOCUMENTS 3,479,545 A    11/1969    Wilson et al.
4,935,624 A    6/1990    Henion et al.
(Continued)

FOREIGN PATENT DOCUMENTS

EP    1 855 306    11/2007
JP    2004-264043    9/2004
(Continued)

OTHER PUBLICATIONS

Asano et al. "Self-aspirating atmospheric pressure chemical ionization source for direct sampling of analysis on surfaces in liquid solution", Rapid Communications in Mass Spectrometry. 2005.
(Continued)

*Primary Examiner* — Nicole Ippolito
*Assistant Examiner* — Hanway Chang
(74) *Attorney, Agent, or Firm* — Knobbe, Martens, Olson & Bear, LLP

(57) ABSTRACT

According to some embodiments, systems and methods for rapid evaporation of liquid phase samples are provided. The method includes directing liquid samples to a thermal evaporation ionizing device, thermally evaporating the liquid samples to create gaseous molecular ions, and directing the gaseous molecular ions to an ion analyzer to analyze and provide information regarding the chemical composition of the liquid samples.

10 Claims, 11 Drawing Sheets

Related U.S. Application Data

(60) Provisional application No. 61/580,723, filed on Dec. 28, 2011.

(51) Int. Cl.
    *G01N 33/493*      (2006.01)
    *H01J 49/04*      (2006.01)
    *G01N 30/72*      (2006.01)
    *H01J 49/00*      (2006.01)
    *A61B 5/20*      (2006.01)
    *A61B 5/00*      (2006.01)

(52) U.S. Cl.
    CPC ......... *A61B 5/4866* (2013.01); *G01N 27/622* (2013.01); *G01N 30/7253* (2013.01); *G01N 33/493* (2013.01); *H01J 49/0031* (2013.01); *H01J 49/0431* (2013.01)

(58) Field of Classification Search
    CPC . G01N 27/622; G01N 30/7253; G01N 33/493
    USPC .... 250/281, 282, 285, 288, 423 R, 424, 425
    See application file for complete search history.

(56) References Cited

U.S. PATENT DOCUMENTS

| | | |
|---|---|---|
| 5,559,326 A | 9/1996 | Goodley et al. |
| 5,756,995 A | 5/1998 | Maswadeh et al. |
| 5,869,344 A | 2/1999 | Linforth et al. |
| 6,531,318 B1 | 3/2003 | Palmer-Toy et al. |
| 6,825,464 B2 | 11/2004 | De La Mora |
| 6,838,663 B2 | 1/2005 | Coon et al. |
| 6,998,622 B1 | 2/2006 | Wang |
| 7,161,144 B2 | 1/2007 | Syage et al. |
| 7,335,897 B2 | 2/2008 | Takats et al. |
| 7,564,028 B2 | 7/2009 | Vestal |
| 7,687,772 B2 | 3/2010 | Shiea |
| 7,718,958 B2 | 5/2010 | Shiea et al. |
| 7,828,948 B1 | 11/2010 | Hatch et al. |
| 7,928,364 B2 | 4/2011 | Musselman |
| 8,193,487 B2 | 6/2012 | Briglin et al. |
| 8,203,117 B2 | 6/2012 | Wiseman et al. |
| 8,232,520 B2 | 7/2012 | Cristoni |
| 8,253,098 B2 | 8/2012 | Hiraoka et al. |
| 8,286,260 B2 | 10/2012 | Vertes et al. |
| 8,314,382 B2 | 11/2012 | Takats |
| 8,324,570 B2 | 12/2012 | Wiseman et al. |
| 8,334,504 B2 | 12/2012 | Finlay |
| 8,395,116 B2 | 3/2013 | Harada et al. |
| 8,481,922 B2 | 7/2013 | Musselman |
| 8,778,695 B2 | 7/2014 | Caprioli |
| 8,803,085 B2 | 8/2014 | Ouyang et al. |
| 8,834,462 B2 | 9/2014 | Johnson |
| 9,046,448 B2 | 6/2015 | Takats |
| 9,281,174 B2 * | 3/2016 | Takats ............... G01N 30/7253 |
| 2002/0008871 A1 | 1/2002 | Poustka |
| 2002/0070338 A1 | 6/2002 | Loboda |
| 2002/0076824 A1 | 6/2002 | Haglund, Jr. et al. |
| 2003/0008404 A1 | 1/2003 | Tomita et al. |
| 2003/0119193 A1 | 6/2003 | Hess et al. |
| 2003/0193023 A1 | 10/2003 | Marsh |
| 2004/0007673 A1 | 1/2004 | Coon et al. |
| 2004/0124352 A1 | 7/2004 | Kashima et al. |
| 2004/0235395 A1 | 11/2004 | Hashish et al. |
| 2005/0017091 A1 | 1/2005 | Olsen et al. |
| 2005/0032471 A1 | 2/2005 | Pfarr et al. |
| 2005/0072916 A1 | 4/2005 | Park |
| 2005/0074361 A1 | 4/2005 | Tanoshima et al. |
| 2005/0077644 A1 | 4/2005 | Bryan et al. |
| 2005/0138861 A1 | 6/2005 | O'Connor |
| 2005/0154490 A1 | 7/2005 | Blaine et al. |
| 2005/0159765 A1 | 7/2005 | Moutafis et al. |
| 2005/0178962 A1 | 8/2005 | Guevremont et al. |
| 2005/0230635 A1 | 10/2005 | Takats et al. |
| 2005/0258358 A1 | 11/2005 | Thakur |
| 2006/0035570 A1 | 2/2006 | Chisum et al. |
| 2006/0091308 A1 | 5/2006 | Boyle et al. |
| 2006/0097084 A1 | 5/2006 | Gromer et al. |
| 2006/0108539 A1 | 5/2006 | Franzen |
| 2006/0122593 A1 | 6/2006 | Jun |
| 2006/0145089 A1 | 7/2006 | Cristoni |
| 2006/0186334 A1 | 8/2006 | Jolliffe et al. |
| 2006/0250138 A1 | 11/2006 | Sparkman et al. |
| 2006/0255264 A1 | 11/2006 | Belford |
| 2007/0023631 A1 | 2/2007 | Takats |
| 2007/0023677 A1 | 2/2007 | Perkins et al. |
| 2007/0094389 A1 | 4/2007 | Nussey et al. |
| 2007/0110666 A1 | 5/2007 | Pevsner et al. |
| 2007/0114437 A1 | 5/2007 | Kovtoun |
| 2007/0176113 A1 | 8/2007 | Shiea |
| 2008/0001081 A1 | 1/2008 | Jindai et al. |
| 2008/0067352 A1 | 3/2008 | Wang |
| 2008/0149822 A1 | 6/2008 | Vertes et al. |
| 2008/0172075 A1 | 7/2008 | Ammann |
| 2008/0173809 A1 | 7/2008 | Wu |
| 2008/0234579 A1 | 9/2008 | Halevy-Politch et al. |
| 2008/0262321 A1 | 10/2008 | Erad et al. |
| 2008/0312651 A1 | 12/2008 | Pope et al. |
| 2009/0065714 A1 | 3/2009 | Keady |
| 2009/0302211 A1 | 12/2009 | Takats |
| 2010/0078550 A1 | 4/2010 | Wiseman et al. |
| 2010/0096546 A1 | 4/2010 | Ewing et al. |
| 2010/0186524 A1 | 7/2010 | Ariessohn |
| 2010/0280409 A1 | 11/2010 | Mark |
| 2011/0036978 A1 | 2/2011 | Franzen |
| 2011/0049352 A1 | 3/2011 | Ding |
| 2011/0152759 A1 | 6/2011 | Clymer et al. |
| 2011/0215233 A1 | 9/2011 | Vertes et al. |
| 2012/0080592 A1 | 4/2012 | Wiseman |
| 2012/0112057 A1 | 5/2012 | Musselman |
| 2012/0156712 A1 | 6/2012 | Takats |
| 2013/0082172 A1 | 4/2013 | Syage et al. |

FOREIGN PATENT DOCUMENTS

| | | |
|---|---|---|
| JP | 2004/529341 | 9/2004 |
| JP | 2005-527786 | 9/2005 |
| JP | 2005-539199 | 12/2005 |
| JP | 2007-513695 | 5/2007 |
| JP | 2007-170870 | 7/2007 |
| JP | 2008-147165 | 6/2008 |
| JP | 2009-539093 | 11/2009 |
| JP | 2009-539114 | 11/2009 |
| JP | 2011/112521 | 6/2011 |
| JP | 2012-505519 | 3/2012 |
| WO | WO 85/04093 | 9/1985 |
| WO | WO 2004/113905 | 12/2004 |
| WO | WO 2005/094389 | 10/2005 |
| WO | WO 2006/081240 | 8/2006 |
| WO | WO 2007/138371 | 12/2007 |
| WO | WO 2007/140351 | 12/2007 |
| WO | WO 2009/157312 | 12/2009 |
| WO | WO 2012/061143 | 5/2012 |
| WO | WO 2012/164312 | 12/2012 |

OTHER PUBLICATIONS

Australian Office Action dated Dec. 10, 2013, Australia Patent Application No. 2010252652, 3pages.

Balog et al., "Identification of Biological Tissues by Rapid Evaporative Ionization Mass Spectrometry", Analytical Chemistry. vol. 82. No. 17, pp. 7343-7350, 2010.

Berkel, "Thin-Layer Chromatography and Electrospray Mass Spectrometry Coupled Using a Surface Sampling probe", Anal. Chem. 2002.

Chen et al., "Neutral Desorption Sampling Coupled to Extractive Electrospray Ionization Mass Spectrometry for Rapid Differentiation of Biosamples by Metabolomic Finger Printing", Journal of Mass Spectrometry, vol. 42, No. 9, pp. 1123-1135 2007.

Guenther et al., "Electrospray Post-Ionization Mass Spectrometry of Electrosurgical Aerosols", Journal of American Society of Mass Spectrometry, vol. 22, No. 11, pp. 2082-2089, 2011.

(56) References Cited

OTHER PUBLICATIONS

Hensman et al., "Chemical Composition of Smoke Produced by High-Frequency Electrospray in a Closed Gaseous Environment an in Vitro Study", Surgical Endoscopy, vol. 12, No. 8, pp. 1017-1019, 1998.
Office Action in Chinese Patent Application No. 201280069258.6 dated Feb. 24, 2016 in 15 pages.
PCT International Search Report and Written Opinion for International Appln. No. PCT/IB2012/002995 dated Sep. 10. 2013, 3 pages.
Al Sahaf, O. S., et al. "Chemical composition of smoke produced by high-frequency electrosurgery." Irish journal of medical science 176.3 (2007): 229-232.
Barrett, William L., and Shawn M. Garber. "Surgical smoke: a review of the literature." Surgical endoscopy 17.6 (2003): 979-987.
Down, S., "A DESI-rable ionization revolutionizes mass spectrometry", Base Peak, Aug. 15, 2005.
International Search Report, for International Application No. PCT/IB2012/002995, dated Sep.10, 2013 (3 pages).
Lee et al., "Thermally Assisted Electrospray Interface for Liquid Chromatography/Mass Spectrometry," Rapid Commun. Mass Spectrom. 1992, 6:727-733.
Liang Qiao et al., "Electrostatic-Spray Ionization Mass Spectrometry," Analytical Chemistry, vol. 84, No. 17, Sep. 4, 2012, pp. 7422-7430.
McEwen et al., "Analysis of Solids, Liquids, and Biological Tissues Using Solids Probe Introduction at Atmospheric Pressure on Commercial LC/MS Instruments," Anal. Chem. 2005, 77:7826-7831.
Moot, et al. "Composition of Volatile Organic Compounds in Diathermy Plume as Detected by Selected Ion Flow Tube Mass Spectrometry," ANZ Journal of Surgery, 2007, vol. 77, pp. 20-23 in 4 pages.
PCT International Search Report dated Aug. 14, 2013 in PCT App. No. PCT/IB2012/003009 in 6 pages.
PCT International Search Report and Written Opinion for International Appln No. PCT/IB2012/003009, dated Aug. 14, 2013, 6 pages.
PCT International Search Report for International Appln No. PCT/IB2010/001261, dated Sep. 30, 2010, 5 pages.
Qiao, Liang, et al. "Electrostatic-spray ionization mass spectrometry." Analytical chemistry 84.17 (2012): 7422-7430.
Sakairi et al., "Characteristics of a Liquid Chromatograph/Atmospheric Pressure Ionization Mass Spectrometer," Anal. Chem. 1988, 60:774-780.
Takats et al., "Characterization of DESI-FTICR mass spectrometry—from ECD to accurate mass tissue analysis," J. Mass Spectrom. 2008, 43:196-203, published online Oct. 8, 2007.
Takats, Z. et al., "Mass spectrometry Sampling under Ambient Conditions with Desorption Electrospray Ionization", Science, Oct. 15, 2004, vol. 306.
Tottszer et al., "laser heating versus resistive heating in the field-desorption mass spectrometry of organic polymers," J. Phys. D: Appl. Phys. 1988, 21:1713-1720.
Written Opinion of the International Searching Authority, for International Application No. PCT/IB2012/002995, dated Sep. 10, 2013 (6 pages).
Japanese Office Action in Japanese patent application No. 2014-549558 dated Aug. 29, 2016 in 4 pages.
Chinese Office Action in Chinese patent application No. 201280069258.6 dated Oct. 25, 2016 in 13 pages.

\* cited by examiner

SYSTEM AND METHOD FOR RAPID EVAPORATIVE IONIZATION OF LIQUID PHASE SAMPLES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present invention relates to devices, systems and methods for quantifying, analyzing and/or identifying chemical species. More specifically, the present invention relates to devices, systems and methods for analyzing chemical species through mass spectrometry or ion mobility spectrometry.

Description of the Related Art

Components of liquid samples are traditionally converted to gaseous ions by either a single step process or a two-step process. Representative examples of a single step system include both desorption ionization and spray ionization methods. Briefly, spray ionization entails a continuous flow of sample which is nebulized by either electrostatic nebulization or pneumatic nebulization (or alternatively, a combination of both electrostatic and pneumatic nebulization). The resulting electrically charged droplets are converted to gaseous ions through solvent evaporation. A representative example of a two-step process is conventional evaporation (i.e., thermodynamically controlled, slow evaporation) followed by gas-phase ionization. Gas-phase ionization is a necessary part of the two-step process because conventional evaporation does not result in the generation of gaseous molecular ions because it is simply too slow. Each of these methods has inherent limitations and/or disadvantages. Conventional evaporation followed by gas-phase ionization has the obvious disadvantage that not all potential analyte molecules can be evaporated: many species of analyte molecules (with a special emphasis on biomolecules) cannot be transferred to a gas phase without subsequent decomposition. Desorption ionization usually requires the drying of liquid samples and therefore cannot be directly used for real-time analysis of continuous sample flow. Spray ionization is currently the most viable method of converting liquid samples into gaseous ions. However, even this method suffers from several limitations, including: its inability to effectively convert fluid samples containing solid, floating material; its inability to accept a wide array of sample liquid viscosities; its inability to accept high concentrations of organic or inorganic salts in fluid samples (such as phosphate buffers or sodium chloride); and lastly its inability to effectively deal with high chemical complexity fluid samples.

Accordingly, there is a need for improved devices, systems and methods for converting liquid samples into gaseous ions.

SUMMARY

In accordance with one embodiment, a method for analyzing liquid phase samples is provided. The method comprises guiding a liquid sample to an ionizing device and thermally evaporating the liquid sample with the ionizing device at a rate sufficient to convert one or more molecular components of the liquid sample to one or more gaseous ions and neutral particles.

In accordance with another embodiment, a system for analyzing liquid phase samples is provided. The system comprises a conduit configured to guide a liquid sample therethrough. The system further comprises a thermal evaporation ionizing device configured to receive the liquid sample from the conduit, the ionizing device configured to thermally evaporate the liquid sample at a rate sufficient to convert one or more molecular components of the liquid sample into one or more gaseous ions and neutral particles. The system further comprises a transport device configured to receive the one or more gaseous ions from the ionizing device.

In accordance with another embodiment, a system for analyzing liquid phase samples is provided. The system comprises a microtiter plate comprising a one or more microwells configured to receive a liquid sample therein. The system further comprises a thermal evaporation ionizing device comprising a pair of electrodes defining a gap therebetween, at least a portion of the electrodes configured to be submerged in the liquid sample and configured to thermally evaporate the liquid sample at a rate sufficient to convert one or more molecular components of the liquid sample into one or more gaseous ions and neutral particles. The system further comprises a conduit configured to receive the one or more gaseous ions from the ionizing device.

DETAILED DESCRIPTION

Figure 1:
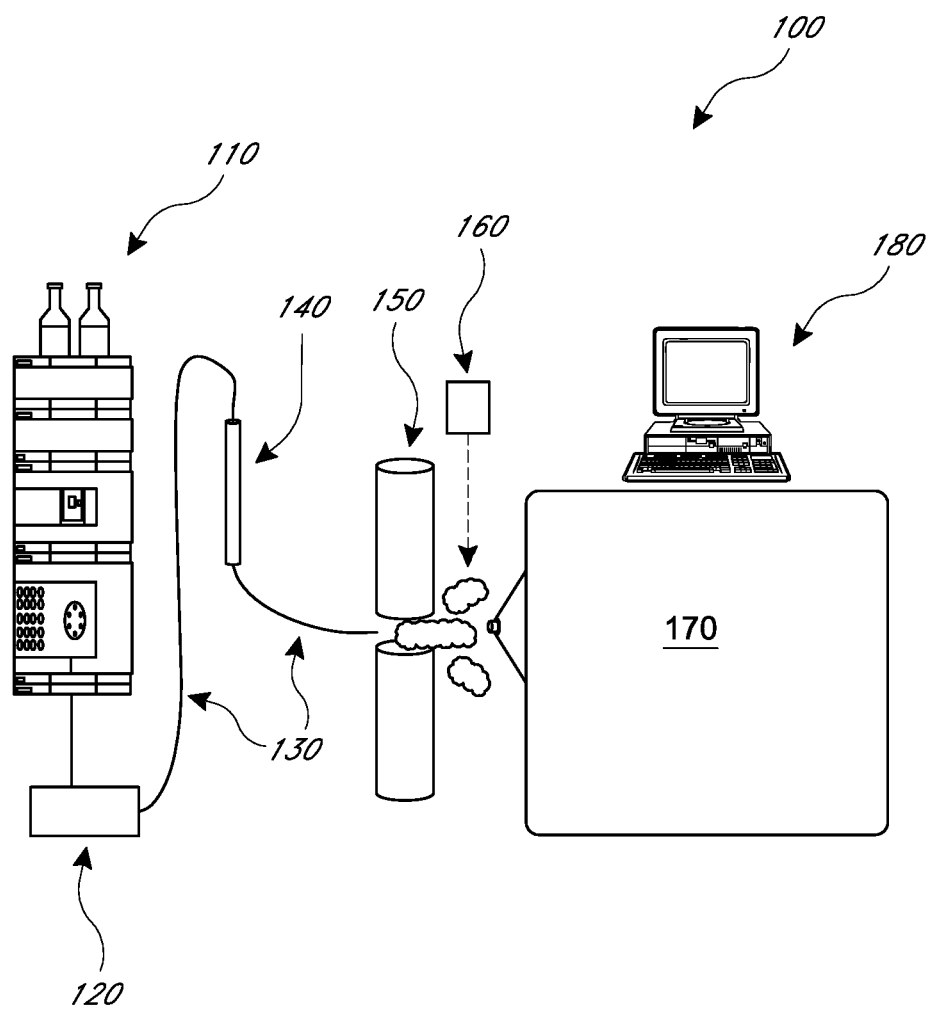
FIG. 1 is a schematic view of one embodiment of a system for converting a liquid phase sample into gaseous ions and for analyzing the gaseous ions.

FIG. 1 illustrates one embodiment of a system for liquid rapid evaporative ionization mass spectrometry (liquid REIMS) 100. The first embodiment of a system for liquid REIMS 100 can include a sample preparation device, a liquid pump that supplies carrier liquid 110, an injector device 120, a liquid transfer system 130, a chromatographic column 140, a thermal evaporation ionizing device 150, a post ionization device 160, an ion analyzer device 170, and a data analysis device 180. In another embodiment, the liquid REIMS system 100 can exclude the post ionization device 160. In still another embodiment, the system 100 can exclude the sample preparation device, liquid pump that supplies carrier liquid 110, injector device 120, chromatographic column 140, or post ionization device 160.

With continued reference to FIG. 1, the liquid pump that supplies carrier liquid 110 is in fluid communication with the injector device 120 and the chromatographic column 140 through the liquid transfer system 130. In other words, the liquid transfer system 130 connects the liquid pump that supplies carrier liquid 110, the injector device 120, and the chromatographic column 140, placing all three devices in fluid communication. The liquid transfer system 130 (e.g., conduit) can terminate approximately at an inlet of the thermal evaporation ionizing device 150 and can deposit any fluid which may be pumped through it into the thermal evaporation ionizing device 150. The post ionization device 160 is placed between the thermal evaporation ionizing device 150 and the ion analyzer device 170. The ion analyzer device 170 and data analysis device 180 can be in data communication (e.g., wired or wireless communication such as radiofrequency communication).

In operation, a user may insert a fluid sample into the sample preparation device. The liquid sample, once prepared in the sample preparation device, can then be introduced via the injector device 120, and be subsequently combined with carrier fluid introduced via the liquid pump that supplies carrier liquid 110 through the liquid transfer system 130 (e.g., conduit). The injector device 120 injects the fluid sample and carrier liquid into the chromatographic column 140 via the liquid transfer system 130. The chromatographic column 140 emits the fluid sample in a time-resolved manner through the liquid transfer system 130. The liquid transfer system 130 then takes the fully prepared fluid sample to the thermal evaporation ionizing device 150 where the liquid transfer system 130 terminates, allowing the fully prepared fluid sample to exit the liquid transfer system 130 and enter the thermal evaporation ionizing device 150. The thermal evaporation ionizing device 150 converts the fully prepared fluid sample into a gaseous state (e.g., produces a fully prepared gaseous sample). The fully prepared gaseous sample may contain some charged particles and some neutral particles. In one embodiment, the fully prepared gaseous sample can then passes through the post ionization device 160 to reach the ion analyzer device 170 where it is analyzed. The data generated by the ion analyzer device 170 during the analysis of the fully prepared gaseous sample is then analyzed by the data analysis device 180.

In some embodiments, the liquid pump that supplies carrier liquid 110 can establish liquid flow for the transfer of the fluid sample through the portion of the liquid REIMS systems 100 upstream of the thermal evaporation ionizing device 150. In some embodiments, the liquid pump that supplies carrier liquid 110 provides constant flow of a carrier fluid during operation of the liquid REIMS system 100. In these embodiments, a liquid sample may be introduced into the system at the injector device 120 into the constant flow provided by the liquid pump that supplies carrier liquid 110. In some embodiments, the liquid pump that supplies carrier liquid 110 establishes constant liquid flow through the system. Such constant flow may include constant positive flow rates (taking sample from the injector device 120 to the thermal evaporation ionizing device 150), which by definition also includes zero-flow (complete sample arrest). In other embodiments, the liquid pump that supplies carrier liquid 110 can establish variable flow rates which may be keyed to the type of sample introduced into the liquid REIMS systems 100. By extension, the liquid pump that supplies carrier liquid 110 may also provide for the intermittent flow of sample throughout the liquid REIMS systems 100 (e.g., once the carrier fluid is combined with the liquid sample introduced via the injector device 120). Flow rate over time of intermittent flow created by a constant flow rate pump may appear to be a square wave. It should be appreciated that the lesser half of the square wave representing flow rate over time need not necessarily drop to zero flow; any greater constant flow rate and any lesser constant flow rate may be used. By extension, flow rate over time of a variable flow rate pump may appear to be sinusoidal. Again, it should be appreciated that the lesser half of the sinusoid (or any other wave representing flow rate over time) need not necessarily drop to zero flow; any variable flow rate and any lesser variable flow rate may be used.

In other embodiments, the liquid pump that supplies carrier liquid 110 may be any other type of pump, including as representative examples not intended to be limiting, syringe pumps, membrane pumps, piston pumps, electrokinetic pumps, pumps employing Venturi's principle, manual pumps, controller modulated pumps, or any other mechanism that generates and sustains a constant or stable flow rate, such as gravitational pumps or vacuum pumps.

The sample preparation device may prepare the sample prior to injection into the liquid REIMS system 100 via the injector device 120. In some embodiments, the preparatory effect of the sample preparation device is to purify the sample. Here, the sample preparation device may be any purifying modality, such as high performance liquid chromatography (HPLC). In other embodiments, the preparatory effect of the sample preparation device is to separate the fluid sample into separate constituents which may be injected through the system in a time-resolved manner. Here, the sample preparation device may be any device capable of separating the sample into separate constituents in a time-resolved manner, including but not limited to solid phase extraction devices, liquid chromatographs, and electrophoretic devices. It should be understood that any sample preparation device may be used singly or in concert: if purity is desires, a purifying modality may be used; if time-gating is desired, a time-gating modality may be used; if purity and time-gating are desired, a purifying modality may be used, followed in sequence by a time-gating modality. Any appropriate sample preparation device may be used at this step.

In some embodiments, the liquid pump that supplies carrier liquid 110 may provide a carrier fluid which can be used to provide a transfer medium for the constituents of the liquid sample through the injector device 120, chromatographic column 140 by way of the liquid transfer system 130 to the thermal evaporation ionizing device 150. The carrier fluid may be incorporated into the sample prior to its insertion into the liquid REIMS systems 100. Alternatively, in other embodiments, the sample preparation device may provide for incorporation of the carrier fluid into the sample automatically prior to introduction of the liquid sample via the injector device 120. Lastly, as mentioned above, the liquid pump that supplies carrier liquid 110 may pump the carrier fluid to the injector device 120 where the liquid sample is introduced. In embodiments where the sample preparation device provides for automatic incorporation of carrier fluid into the liquid sample, the sample preparation device includes a reservoir of carrier fluid which it combines with the liquid sample in an appropriate carrier fluid to liquid sample ratio. Carrier fluid may be incorporated prior to sample preparation (and go through the sample preparation process with the sample fluid), or it may be incorporated after the sample preparation has been completed.

In some embodiments, the carrier fluid is composed of a single solvent or mixture of various solvents. The carrier fluid can facilitate movement of the sample fluid from insertion into and exit from the liquid transfer system 130 at the thermal evaporation ionizing device 150. Therefore, in some embodiments, the carrier fluid has such properties that substantially full evaporation without the formation of significant solid residues is possible upon passing through the thermal evaporation ionizing device 150. Moreover, in one embodiment, the carrier fluid can evaporate in the thermal evaporation ionizing device 150 at a rate greater than or equal to the rate of evaporation of the sample fluid. In embodiments in which the thermal evaporation ionizing device 150 employs Joule-heating to vaporize the sample fluid (as will be discussed below) the carrier fluid is advantageously electrically conductive (such as an aqueous solvent system).

In some embodiments, the liquid transfer system 130 is an open tubular element which functions as a fluid conduit between the functional parts of the liquid REIMS systems 100, including the liquid pump that supplies carrier liquid 110, the injector device 120, the chromatographic column 140 and the thermal evaporation ionizing device 150. The liquid transfer system 130 provides for fluid communication between the aforementioned components. In some embodiments, the liquid transfer system 130 can be constructed out of any appropriate plastic, such as polyetheretherketone (PEEK) or polytetrafluoroethylene (PTFE). In other embodiments, the liquid transfer system 130 is constructed out of stainless steel, fused silica, or other suitable materials.

In some embodiments, the liquid transfer system 130 can be made of any material with sufficient mechanical strength, chemical stability, and sufficiently high flexibility for use in a liquid rapid evaporation mass spectroscopy system. For example, the liquid transfer system 130 can be made out of various polymers, (e.g., polyethylene, polytetrafluoroethylene, polypropylene, polyvinylchloride), metals (e.g., steel, copper), glass and fused silica. In some embodiments, the liquid transfer system 130 has low porosity and is inert. In one embodiment, the tube wall advantageously neither retains neither charged nor neutral gaseous particles, nor interacts with such species or facilitates their chemical reactions.

In some embodiments, the internal diameter of the liquid transfer system 130 (e.g., of a conduit of the liquid transfer system 130) is anywhere between about 0.1-20 mm, about 0.5-10 mm, and about 1.0-2.0 mm, including 1.5 mm, or any other diameter needed to transport fluid throughout the system. In one embodiment, the internal diameter is as small as possible to advantageously aid in the detection speed of the fluid and ions of interest.

In some embodiments, the length of the liquid transfer system 130 can be anywhere between about 0-5000 mm, about 0-4000 mm, about 0-3000 mm, about 0-2000 mm, about 0-1000 mm, about 0-500 mm, and about 0-250 mm, including about 100 mm. Other suitable lengths can be used.

The liquid transfer system 130 can be used at ambient temperature, or at elevated temperatures. In some embodiments, operating temperatures can be set anywhere between ambient and 400° C. Higher operating temperatures may advantageously shift the adsorption-desorption equilibrium taking place on the wall surfaces of the liquid transfer system 130 towards desorption, thereby suppressing undesired memory effects. Additionally, elevated temperatures can also advantageously shift gas-phase association-dissociation equilibrium towards dissociation, which decreases the recombination rate of ionic species with opposite charges.

In some embodiments, the liquid transfer system 130 contains porous or fibrous material (glass wool, fabric, etc.) to irreversibly capture large particles not producing individual gaseous ions.

In some embodiments, the chromatographic column 140 is a liquid chromatographic column used to separate components of the fluid sample in a time-resolved manner. The chromatographic column 140 may be replaced by any other device capable of separating a fluid sample into time-resolved constituents, including but not limited to solid phase extraction devices and electrophoretic devices.

In some embodiments, the chromatographic column 140 is a separate element from the sample preparation device, decoupled from the sample preparation device.

In other embodiments, the chromatographic column 140 is coupled with or included in the sample preparation device (e.g., where the sample preparation device is upstream of the injector device 120). In yet other embodiments, in which time-resolution of certain constituents is not desirable, the chromatographic column 140 may be omitted entirely from the liquid REIMS systems 100.

In some embodiments, prior to evaporation in the thermal evaporation ionizing device 150, the sample is subjected to a non-destructive analysis. Some representative examples of non-destructive sample analysis include colorimetry, electrochemical analysis, optical spectroscopy, nuclear magnetic resonance spectroscopy or any other method which does not fully consume the liquid sample. In some embodiments, the non-destructive analysis is done in a flow-through mode. In other embodiments, the non-destructive analysis is done through division of the sample.

In some embodiments, the injector device 120 is used broadly to introduce the fluid sample into the thermal evaporation ionizing device 150. Generally speaking, the injector device 120 is in fluid communication with the liquid pump that supplies carrier liquid 110 and chromatographic column 140 via the liquid transfer system 130 and can provide for a carefully modulated injection of the sample fluid into the thermal evaporation ionizing device 150 through the liquid transfer system 130. The injector device 120 may be a loop injector as is used in commercial liquid chromatographic embodiments/applications, though other suitable injectors can be used. In some embodiments, the injector device 120 can be placed between the sample preparation device and the chromatographic column 140. In other embodiments, the injector device 120 is placed between the chromatographic column 140 and the thermal evaporation ionizing device 150. In some embodiments, the flow rate of sample fluid (or a mixture of sample fluid and carrier fluid) into the thermal evaporation ionizing device is in the range of about 1 nl/min-10 L/min, about 10 nl/min-1 L/min, about 100 nl/min-100 ml/min, about 1 µl/min-10 ml/min, about 10 µl/min-1 ml/min, about 1 nl/min-100 nl/min, and about 1 ml/min-10 ml/min. In some embodiments, the flow rate is optimized based on parameters of the liquid REIMS system 100 (e.g., type of thermal evaporation ionizing device 150 used, power applied to the thermal evaporation ionizing device 150, sample fluid viscosity, sample fluid surface tension, etc) to advantageously address and evaporate substantially all of the sample fluid, thereby preventing sample loss.

In some embodiments, the thermal evaporation ionizing device 150 converts certain molecular components of the liquid sample into gaseous ions. The thermal evaporation ionizing device 150 may thermally evaporate at least a part of the liquid sample and aerosolize the remaining part thereby resulting in a gaseous sample containing molecules, clusters, and droplets. In some embodiments, the thermal evaporation ionizing device 150 evaporates substantially all of the liquid sample (e.g., rate of evaporation is substantially equal to the flow rate out of the liquid transfer system 130). In other embodiments, the thermal evaporation ionizing device 150 advantageously evaporates only part of the liquid sample (e.g., where the liquid sample has high salt concentration). The range of evaporation rates of the thermal evaporation ionizing device 150 are sufficient to convert one or more molecular components of the liquid sample to one or more gaseous ions. Such thermal evaporation may be effected by contact heating, heating by electric current, heating by electromagnetic radiation, or any other type of rapid heating. The conversion of the liquid sample from its liquid state to its gaseous state results in the desired gaseous ionic species.

In some embodiments, ion production at the thermal evaporation ionizing device 150 can be improved by applying an electrostatic potential between the thermal evaporation ionizing device 150 and the inlet of the ion analyzer device 170. The resulting droplets may thus carry a net electric charge, thereby increasing the number of ions formed.

In some embodiments, the post ionization device 160 (e.g., secondary ion source) functions to improve ion production after the conversion from liquid into gas by the thermal evaporation ionizing device 150 (and concomitant ion production by the thermal evaporation ionizing device 150). The post ionization device 160 may be any ion source that can produce a sufficiently high current of ions. The ions created by the post ionization device 160 interact with the neutral particles produced by the thermal evaporation ionizing device 150 via electric charge transfer reactions thereby creating ionized species capable of being detected and analyzed by the ion analyzer device 170. In some embodiments, the post ionization device 160 is an electrospray post ionization device in which a pure solvent is electrosprayed into the aerosol particles of the liquid sample created by the thermal evaporation ionizing device 150. The pure solvent electrosprayed as multiply charged droplets merges with the aerosol particles of the liquid sample thereby creating ionized species capable of being detected and analyzed by the ion analyzer device 170. Additionally, the electrosprayed solvent may contain molecules which undergo chemical reactions with the components of the sample, thereby generating ions species. In other embodiments, the post ionization device 160 can be a corona discharge ionization source, a glow discharge ionization source, an atmospheric pressure chemical ionization source, a dielectric barrier discharge ionization source, or an electromagnetic ionization source.

In some embodiments, the ion analyzer device 170 separately detects ions by using/detecting one or more of their chemically determined characteristics. In other embodiments, the ion analyzer device 170 separately detects ions by using/detecting one or more of their structurally determined characteristics. In yet other embodiments, the ion analyzer device 170 separately detects ions by using/detecting one of more of a combination of their chemically determined and structurally determined characteristics. For example, the ion analyzer device 170 may be a mass spectrometric analyzer which uses mass-to-charge ratio as its basis for separation. Alternatively, the ion analyzer device 170 may be an ion mobility spectrometry analyzer which uses collisional cross section and charge. In some embodiments, other types of mass analyzers may be used, including, but not limited to any of the various ion trap instruments and time-of-flight analyzers. In one embodiment, the ion analyzer device 170 can be an ion trap instrument and time-of-flight analyzer, both of which when combined advantageously can analyze a fluctuating ion current provided by the thermal evaporation ionizing device 150. The ion analyzer device 170 may generate data resulting from its analysis of the ions produced by the thermal evaporation ionizing device 150 or the thermal evaporation ionizing device 150 and post ionization device 160. Generally, the data generated by the ion analyzer device 170 can be in the form of electronic data, processable by a computer.

In some embodiments, the thermal evaporation ionizing device 150 (or thermal evaporation ionizing device 150 and post ionization device 160) and ion analyzer device 170 can be fully decoupled. In these embodiments, the liquid transfer system 130 delivers the sample fluid in liquid form to the thermal evaporation ionizing device 150 which converts it to its gaseous state which includes some number of ionic species. The gaseous sample can then be conveyed to the ion analyzer device 170 where it is analyzed. The gaseous sample can be conveyed by any of a number of methods, including diffusion or injection pump (similar to the injector device 120) and gas transfer system (similar to the liquid transfer system 130). Ultimately, in such a decoupled system, any device, or combination of devices capable of delivering the gaseous sample ions from the thermal evaporation ionizing device 150 to the ion analyzer device 170 can be used.

In other embodiments, the thermal evaporation ionizing device 150 (or thermal evaporation ionizing device 150 and post ionization device 160) and ion analyzer device 170 can be fully coupled. In these embodiments, the liquid transfer system 130 delivers the sample fluid in liquid form to the thermal evaporation ionizing device 150 which converts it to its gaseous state which includes some number of ionic species. Because the thermal evaporation ionizing device 150 and ion analyzer device 170 are coupled in these embodiments, the gaseous sample can be directly read/analyzed by the ion analyzer device 170 without the need for any of the aforementioned transportation required by a fully decoupled system.

In some embodiments, the data analysis device 180 is a computer and appropriate analysis software. In these embodiments, the data analysis device 180 converts the raw electronic signal generated by the ion analyzer device 170 into analytical information. In some embodiments, the data analysis device 180 includes a device by which the analytical information may be conveyed to a user. In some embodiments, information can be conveyed in the form of full spectra on a screen or in print-outs. In other embodiments, when only a positive/negative response is desired (such as in urine drug testing) information can be conveyed in a binary format, such as by an aural tone for positive, a simple positive/negative result displayed on a monitor or printout, etc. Any of a number of reporting methods can be used depending on the application for the liquid REIMS systems 100.

The liquid REIMS systems 100 have several advantages over currently available systems which render its use highly advantageous in many scenarios. The system disclosed provides for a very easy mass-spectrometric or ion-mobility spectrometric analysis of fluid samples while eliminating the problem of clogging due to the presence of solid, floating material experienced by spray ionization. Additionally the system disclosed herein eliminates problems created by widely varying sample viscosities, high concentrations of either organic or inorganic salts in fluid samples (such as phosphate buffers or sodium chloride), and high degrees of chemical complexity. Moreover, liquid REIMS is particularly well suited to the addition of a secondary ionization source, does not require expensive and sophisticated high-pressure hardware, is compatible with solid phase REIMS systems, permits very rapid sample preparation, and lastly is highly robust.

Figure 2A:
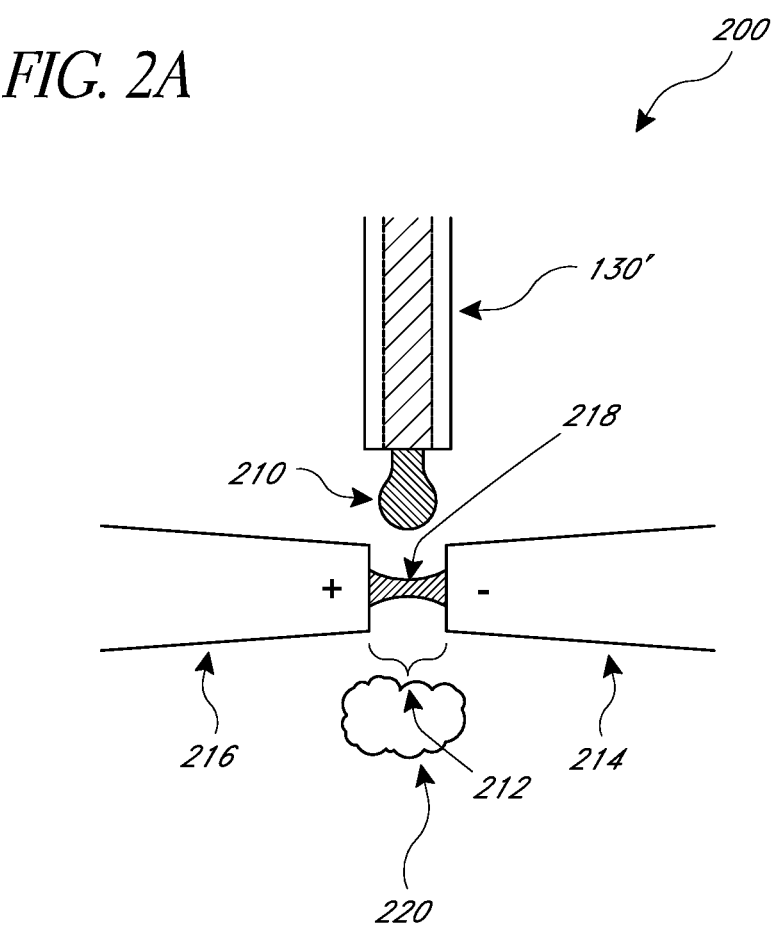
FIG. 2A is a schematic view of one embodiment of an ionizing device system for converting a liquid phase sample into gaseous ions.

FIG. 2A illustrates a two-electrode liquid bridge embodiment of the thermal evaporation ionizing device 200 for use in a liquid REIMS system, such as the liquid REIMS system 100. The two-electrode liquid bridge embodiment of the thermal evaporation ionizing device 200 includes a liquid transfer system 130', sample fluid in liquid state 210, an electrode bridge gap 212 (defined between a first electrode 214 and a second electrode 216—a liquid sample fluid bridge 218 is formed by the passage of the sample fluid in liquid state 210 through the gap between the first electrode 214 and second electrode 216, and sample fluid in gaseous state 220 is generated by passing an electric current through the liquid sample fluid bridge 218), and sample fluid in gaseous state 220.

In some embodiments disclosed herein, the liquid transfer system 130', post ionization device 160', ion analyzer device 170', and the data analysis device 180' can be similar to, or identical to, and used in the same manner as has already been discussed above in connection with the system 100 in FIG. 1.

In operation, the pair of electrodes comprising the first electrode 214 and the second electrode 216 is placed under the terminal end (distal end) of the liquid transfer system 130' (e.g., conduit) and an electrical potential difference is applied to the first electrode 214 and second electrode 216. As it exists the liquid transfer system 130', the sample fluid in liquid state 210 may be pure sample, sample and carrier fluid, or any of the aforementioned released in a time-resolved manner as discussed above. As the sample fluid in liquid state 210 exits the liquid transfer system 130', it passes into the electrode bridge gap 212, thereby providing the liquid sample fluid bridge 218 between the first electrode 214 and second electrode 216. When sufficient sample fluid in liquid state 210 has collected on the liquid sample fluid bridge 218 to complete or close the electric circuit, the resulting electric current partially or completely evaporates the sample fluid in liquid state 210 thereby creating sample fluid in gaseous state 220 and gaseous ions thereof.

In some embodiments, the electrode bridge gap 212 between the first electrode 214 and second electrode 216 is in the range of about 0.1 mm-5 mm, about 0.2-2.5 mm, about 0.3-1.5 mm, and about 0.4-0.75 mm, about 0.5-0.6 mm including about 1 mm. In these embodiments, as mentioned above, if a carrier fluid is used, it may be highly advantageous that the carrier fluid be electrically conductive (such as an aqueous solvent system), to thereby facilitate completion of the electrical circuit between the first electrode 214 and the second electrode 216.

In some embodiments, electrodes with high specific surface areas are used. In such embodiments, the surfaces of the first electrode 214 and the second electrode 216 are roughened either mechanically or electrochemically, or constructed out of a porous material (such as active carbon, metal foam, metal-coated silica, or any other electrically conductive porous material). Alternatively, in other embodiments, electrodes having low specific surface areas are used. In these embodiments, the surfaces of the first electrode 214 and the second electrode 216 are polished to create a smooth surface. Yet other embodiments use sharp needle electrodes to effectively direct current.

In some embodiments, the first electrode 214 and second electrode 216 have cylindrical surfaces with diameters in the range of about 1-10 mm, 2-8 mm, and 3-6 mm, including about 5 mm. In some embodiments, the first electrode 214 and second electrode 216 can have other suitable dimensions. In some embodiments, the first electrode 214 is a negative electrode and the second electrode 216 is a positive electrode. In other embodiments, the first electrode 214 is a positive electrode and the second electrode 216 is a negative electrode.

In some embodiments, the electrical potential difference applied to the first electrode 214 and second electrode 216 is a direct potential difference. In other embodiments, the electrical potential difference applied to the first electrode 214 and the second electrode 216 is an alternating potential difference. In some embodiments, the magnitude of the potential difference applied across the first electrode 214 and the second electrode 216 is in the range of about 10V/mm-100 kV/mm, about 50v/mm-20 kV/mm, about 250v/mm-4 kV/mm, about method for analyzing a liquid sample using liquid rapid evaporative ionization of liquid phase samples 500V/mm-2 kV/mm, and about 750V/mm-1 kV/mm. In some embodiments, the highest voltage possible without discharge through the air is used to advantageously thermally evaporate the liquid sample.

In some embodiments, the flow rate of the sample fluid in liquid state 210 exiting the liquid transfer system 130' is low enough that substantially all of the sample fluid in liquid state 210 exiting the liquid transfer system 130' is vaporized as it enters the electrode bridge gap 212 and creates a liquid sample fluid bridge 218. In some embodiments, the two-electrode liquid bridge embodiment of the thermal evaporation ionizing device 200 evaporates substantially all of the liquid sample (e.g., rate of evaporation is substantially equal to the flow rate out of the liquid transfer system 130'). In some embodiments, the flow rate of sample fluid (or a mixture of sample fluid and carrier fluid) into the thermal evaporation ionizing device is in the range of about 1 nl/min-10 L/min, about 10 nl/min-1 L/min, about 100 nl/min-100 ml/min, about 1 µl/min-10 ml/min, about 10 µl/min-1 ml/min, about 1 nl/min-100 nl/min, and about 1 ml/min-10 ml/min. In some embodiments, the flow rate is optimized based on parameters of the two-electrode liquid bridge embodiment of the thermal evaporation ionizing device 200 (e.g., electrode size, magnitude of the gap between electrodes, power applied to the electrodes, sample fluid viscosity, sample fluid surface tension, etc) to advantageously address and evaporate substantially all of the sample fluid, thereby preventing sample loss. In some embodiments, the two-electrode liquid bridge embodiment of the thermal evaporation ionizing device 200 evaporates only a portion of the liquid sample thereby maintaining fluid flow over the electrodes during operation. The maintenance of constant flow when analyzing samples having high salt concentrations advantageously prevents the build-up of salts on the electrode surfaces. The range of evaporation rates of the two-electrode liquid bridge embodiment of the thermal evaporation ionizing device 200 are sufficient to convert one or more molecular components of the liquid sample to one or more gaseous ions.

In some embodiments in which a liquid sample with a low surface tension is analyzed, both electrodes may be pre-wetted to advantageous aid in the formation of a liquid sample fluid bridge 218.

The sample fluid in gaseous state 220 created by the two-electrode liquid bridge embodiment of the thermal evaporation ionizing device 200 may include gaseous ions, and neutral particles, and may be read/analyzed as described above by the ion analyzer device 170'. In some embodiments, the two-electrode liquid bridge embodiment of the thermal evaporation ionizing device 200 is used advantageously in concert with a post ionization device 160 as described above.

Figure 2B:
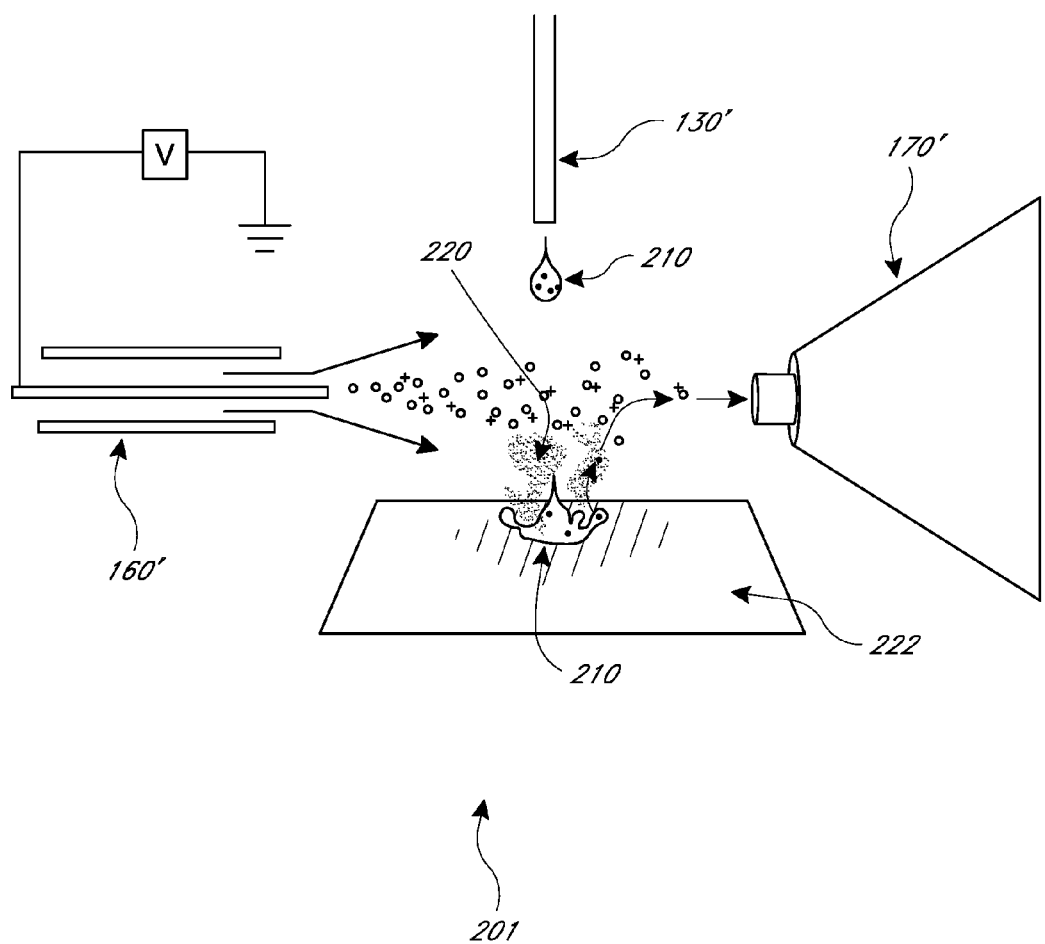
FIG. 2B is a schematic view of another embodiment of an ionizing device system for converting a liquid phase sample into gaseous ions.

FIG. 2B illustrates a hotplate embodiment of a thermal evaporation ionizing device 201 for use in liquid REIMS systems. The hotplate embodiment of the thermal evaporation ionizing device 201 includes a liquid transfer system 130', a post ionization device 160', an ion analyzer device 170', sample fluid in liquid state 210, sample fluid in gaseous state 220, and a hotplate 222.

In operation, the hotplate 222 is placed directly beneath the distal/terminal end of the liquid transfer system 130' and heated. The sample fluid in liquid state 210 exits (e.g., drips from) the liquid transfer system 130' and falls under the guidance of gravity from the distal/terminal end of the liquid transfer system 130' down onto the hotplate 222. As it exists the liquid transfer system 130', the sample fluid in liquid state 210 may be pure sample, sample and carrier fluid, or any of the aforementioned released in a time-resolved manner as discussed above. Upon hitting the hotplate 222, the sample fluid in liquid state 210 rapidly (e.g., nearly instantaneously) evaporates into sample fluid in gaseous state 220. In further operation, a post ionization device 160' is used to increase the rate of ionization of the sample fluid in gaseous state 220. The more completely ionized sample fluid in gaseous state 220 (e.g., which includes gaseous ions) can then detected by the ion analyzer device 170' and read/analyzed.

In some embodiments, during operation, the hotplate 222 is heated to a temperature between the boiling point and the Leidenfrost temperature of the sample fluid in liquid state 210, thereby ensuring the most rapid evaporation possible. In some embodiments, during operation, the hotplate 222 is kept at a temperature substantially higher than the boiling point of the sample fluid but still under the sample fluid's Leidenfrost temperature. In some embodiments, the hotplate 222 includes a spiked surface which may advantageously render it difficult for a droplet to levitate, thereby avoiding the Leidenfrost effect. In other embodiments, the hotplate 222 surface is coarse and or easy to wet (e.g., possessing a low surface tension) which may also have the beneficial effect of aiding in the prevention of the Leidenfrost effect.

In some embodiments, the hotplate 222 is constructed out of a high resistance material, capable of creating high temperatures upon application of electric power. Select examples of possible hotplate 222 materials, not intended to limit the scope of this disclosure, include the following: refractory metals, such as molybdenum, tantalum, tungsten, and nickel-iron; nickel-based alloys, such as nickel-chromium 35-19, nickel-chromium 68-20, nickel-chromium 60-16, nickel-chromium 80-20; iron based alloys, such as iron-aluminum, chromium-aluminum, molybdenum disilicide (including molybdenum doped with aluminum); or others, such as iron-nickel-chromium, aluminum-iron-chromium, Inconel, nickel-tungsten, cermets, silicon carbide, kanthal (FeCrAl), super kanthal, graphite, silicon carbide, positive thermal coefficient of resistance ceramics, platinum. In some embodiments, an atmosphere other than air is used.

In some embodiments, the post ionization device 160' is an electrospray post ionization device. In other embodiments, the post ionization device 160' may be any of the other post ionization devices disclosed above.

In some embodiments, the flow rate of the sample fluid in liquid state 210 exiting the liquid transfer system 130' is low enough that substantially all of the sample fluid in liquid state 210 exiting the liquid transfer system 130' is vaporized as it hits, or substantially immediately after it hits, the hotplate 222. It may be undesirable for a residue of liquid in the form of a jet or droplets to remain unevaporated. In some embodiments, the hotplate embodiment of a thermal evaporation ionizing device 201 evaporates substantially all of the liquid sample (e.g., rate of evaporation is substantially equal to the flow rate out of the liquid transfer system 130'). In other embodiments, the hotplate embodiment of a thermal evaporation ionizing device 201 evaporates less than all of the liquid sample (e.g., where the liquid sample has high salt concentration). The range of evaporation rates of the hotplate embodiment of a thermal evaporation ionizing device 201 are sufficient to convert one or more molecular components of the liquid sample to one or more gaseous ions. In some embodiments, the flow rate is in the range of about 10 nL/min-50 mL/min, about 100 nL/min-5 mL/min, about 1 µL/min-500 µL/min, and about 10 µL/min-50 µL/min including about 100 µL/min. In some embodiments the flow rate is high enough that the liquid sample fluid will not evaporate in the liquid transfer system 130' prior to reaching the hotplate 222. In some embodiments, the flow rate is optimized based on parameters of the hotplate embodiment of a thermal evaporation ionizing device 201 (e.g., hotplate 222 shape, size and surface characteristics, hotplate 222 temperature, sample fluid viscosity, sample fluid surface tension, etc) to advantageously address and evaporate substantially all of the sample fluid, thereby preventing sample loss.

Figure 2C:
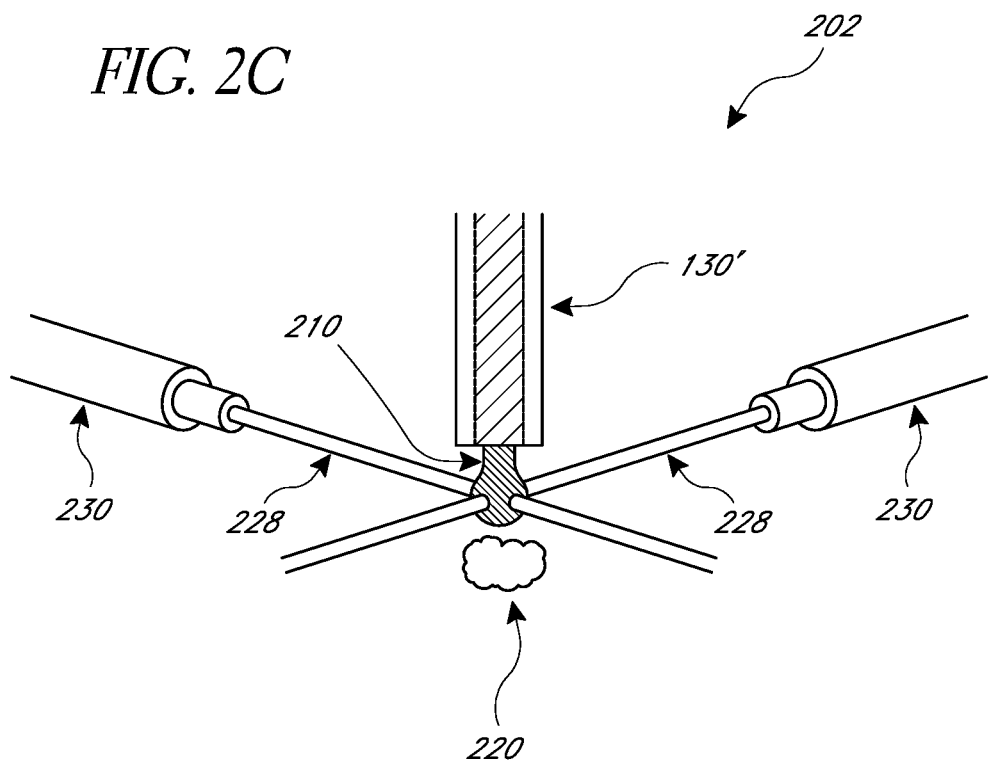
FIG. 2C is a schematic view of still another embodiment of an ionizing device system for converting a liquid phase sample into gaseous ions.

FIG. 2C illustrates a laser embodiment of a thermal evaporation ionizing device 202 for use in a liquid REIMS system. The laser embodiment of the thermal evaporation ionizing device 202 includes a liquid transfer system 130', sample fluid in liquid state 210, sample fluid in gaseous state 220, and at least one electromagnetic radiation beam 228 produced by at least one electromagnetic radiation producing device or laser 230.

In operation, the at least one electromagnetic radiation beam 228 is focused at a location spaced apart from (e.g., directly below) the distal/terminal end of the liquid transfer system 130' (e.g., conduit). In one embodiment, the sample fluid in liquid state 210 exits the liquid transfer system 130' and beads under the guidance of gravity on the distal/terminal end of the liquid transfer system 130' down into the electromagnetic radiation beam 228 focused directly below the distal/terminal end of the liquid transfer system 130'. As it exits the liquid transfer system 130', the sample fluid in liquid state 210 may be pure sample, sample and carrier fluid, or any of the aforementioned released in a time-resolved manner as discussed above. The energy of the at least one electromagnetic radiation beam 228 causes the sample fluid in liquid state 210 to vaporize thereby forming sample fluid in gaseous state 220 (e.g., gaseous ions). The sample fluid in gaseous state 220 created by the laser embodiment of the thermal evaporation ionizing device 202 may be read/analyzed as described above by the ion analyzer device 170'. In some embodiments, the laser embodiment of the thermal evaporation ionizing device 202 may be used advantageously in concert with the post ionization device 160'.

In some embodiments, the electromagnetic radiation beam 228 is a focused beam of electromagnetic radiation. In other embodiments, the electromagnetic radiation beam 228 is a collimated beam of electromagnetic radiation (such as a carbon-dioxide laser). In some embodiments, the laser embodiment of the thermal evaporation ionizing device 202 uses only one electromagnetic radiation beam 228. In other embodiments, the laser embodiment of the thermal evaporation ionizing device 202 uses more than one electromagnetic radiation beam 228, for example, 2 electromagnetic radiation beams 228, 3 electromagnetic radiation beams 228, 4 electromagnetic radiation beams 228, 5 electromagnetic radiation beams 228, or more than 5 electromagnetic radiation beams 228.

In some embodiments, the flow rate of the sample fluid in liquid state 210 exiting the liquid transfer system 130' is low enough that substantially all of the sample fluid in liquid state 210 exiting the liquid transfer system 130' is vaporized as it enters the electromagnetic radiation beam 228 or combination/intersection of more than one electromagnetic radiation beam 228. In some embodiments, the laser embodiment of a thermal evaporation ionizing device 202 evaporates substantially all of the liquid sample (e.g., rate of evaporation is substantially equal to the flow rate out of the liquid transfer system 130'). In other embodiments, the laser embodiment of a thermal evaporation ionizing device 202 evaporates less than all of the liquid sample. The range of evaporation rates of the laser embodiment of a thermal evaporation ionizing device 202 are sufficient to convert one or more molecular components of the liquid sample to one or more gaseous ions. In some embodiments, the flow rate of sample fluid (or a mixture of sample fluid and carrier fluid) into the thermal evaporation ionizing device (e.g., electromagnetic radiation beam 228) is in the range of about 1 nl/min-10 L/min, about 10 nl/min-1 L/min, about 100 nl/min-100 ml/min, about 1 μl/min-10 ml/min, about 10 μl/min-1 ml/min, about 1 nl/min-100 nl/min, and about 1 ml/min-10 ml/min. In some embodiments, the flow rate is optimized based on parameters of the laser embodiment of a thermal evaporation ionizing device 202 (e.g., number of electromagnetic radiation beams 228 used, power of the electromagnetic radiation beams, sample fluid viscosity, sample fluid surface tension, etc) to advantageously address and evaporate substantially all of the sample fluid, thereby preventing sample loss.

Figure 3:
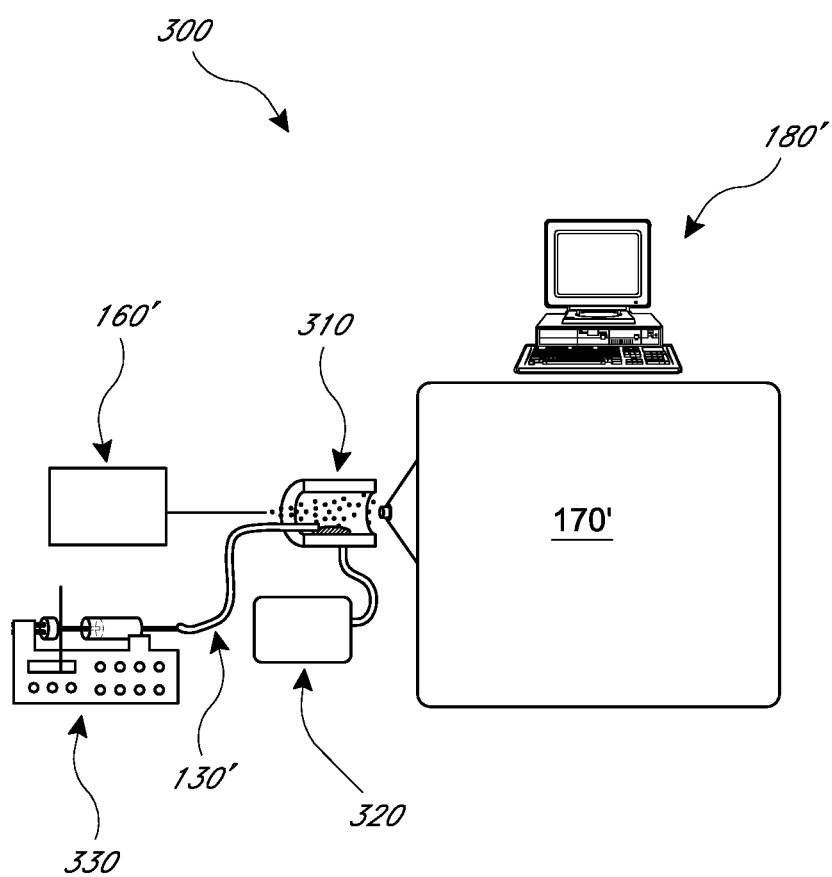
FIG. 3 is a schematic view of another embodiment of a system for converting a liquid phase sample into gaseous ions and for analyzing the gaseous ions.

FIG. 3 illustrates another embodiment of a liquid REIMS system 300. The liquid REIMS system 300 includes a sample fluid pump 330, a liquid transfer system 130', an evaporation cylinder (thermal evaporation ionizing device) 310, an evaporation cylinder control and power source 320, a post ionization device 160', an ion analyzer device 170', and a data analysis device 180. In one embodiment, the liquid transfer system 130' can include a conduit having an outer diameter of 1.5875 mm and an internal diameter of 1.27 mm and be made of PTFE tubing. However, in other embodiments, the liquid transfer system 130' can include a conduit having other suitable dimensions and made of other materials (e.g., plastic materials).

In the illustrated embodiment, the sample fluid pump 330 is in fluid communication with the evaporation cylinder 310 through the liquid transfer system 130'. The evaporation cylinder 310 is in electrical communication with the evaporation cylinder control and power source 320. The post ionization device 160' is placed such that it may ionize or direct charged particles within the interior lumen of the evaporation cylinder 310. The ion analyzer device 170' is placed on the side of the evaporation cylinder 310 opposite to the post ionization device 160'. The data analysis device 180' is in data communication with the ion analyzer device 170'. In one embodiment, the evaporation cylinder 310 can have a length of between about 12.7 mm and about 5.08 cm and an internal diameter of between abut 7.62 mm and about 2.54 cm. In one embodiment, the evaporation cylinder 310 can have a length of about 2.54 cm and an internal diameter of about 12.7 mm. However, the evaporation cylinder 310 can have other suitable lengths and diameters.

In operation, the evaporation cylinder control and power source 320 raises the evaporation cylinder 310 to an appropriate temperature (e.g., via a heater coupled to, attached to or embedded in, the evaporation cylinder 310) after which the sample fluid pump 330 injects sample fluid in its liquid state into the heated evaporation cylinder 310. In one embodiment, the evaporation cylinder 310 (e.g., the internal surface 312 of the evaporation cylinder 310) can be heated to a temperature of between about 150° C. and about 800° C. The fluid sample may run through the sample fluid pump 330 into the liquid transfer system 130'. The liquid transfer system 130' carries the fluid sample from the sample fluid pump 330 to the evaporation cylinder 310 where the liquid transfer system 130 terminates, allowing the fluid sample to exit the liquid transfer system 130 and enter the evaporation cylinder 310, coming in contact with a heated cylindrical inner surface 312 of the evaporation cylinder 310. The heated evaporation cylinder 310 then causes the sample fluid in its liquid state to vaporize from its liquid state into its gaseous state via contact heating. The sample fluid in its gaseous state may contain some charged particles and some neutral particles. In further operation, to increase ionization (the concentration of charged particles), the post ionization device 160' ionizes the sample fluid in its gaseous state which may then be read/analyzed by the ion analyzer device 170'. In one embodiment, the post ionization device 160' could be an electrospray ion source. The ion analyzer device 170' can then communicate the data to the data analysis device 180' to be processed and analyzed.

In some embodiments, the sample fluid pump 330 is a liquid pump which is used to establish liquid flow for the transfer of the fluid sample from the sample fluid pump 330 to the evaporation cylinder 310 through the liquid transfer system 130'. In some embodiments, the liquid pump of the sample fluid pump 330 establishes constant flow through the system. Such constant flow may include constant positive flow rates (taking sample to the evaporation cylinder 310), which by definition it also includes zero-flow (complete sample arrest). In other embodiments, the liquid pump of the sample fluid pump 330 establishes variable flow rates which may be keyed to the type of sample introduced into liquid REIMS system 300. By extension, the liquid pump may also provide for the intermittent flow of sample throughout the liquid REIMS system 300. As discussed above, flow rate over time of intermittent flow created by a constant flow rate pump may appear to be a square wave. It should be appreciated that the lesser half of the square wave representing flow rate over time need not necessarily drop to zero flow: any greater constant flow rate and any lesser constant flow rate may be used. By extension, flow rate over time of a variable flow rate pump may appear to be sinusoidal. Again, it should be appreciated that the lesser half of the sinusoid (or any other wave representing flow rate over time) need not necessarily drop to zero flow; any variable flow rate and any lesser variable flow rate may be used.

In some embodiments, the sample fluid pump 330 is a manual pump by which a user may manually inject a sample into the evaporation cylinder 310. For example, in some embodiments such a manual pump is a syringe which may be coupled directly to the liquid transfer system 130' by threads or other suitable mechanisms. Here, in operation, a user may aspirate a fixed volume of the desired sample (for example a urine sample to conduct a urine toxicology test) from a liquid sample container using a syringe then couple that syringe to the liquid transfer system 130' by any appropriate mechanism (for example by threads or a spring lock) then selectively depress the syringe's plunger to inject the sample into the evaporation cylinder 310. In some embodiments of the sample fluid pump 330 in which a syringe pump is used, the syringe pump may be actuated by a controller (e.g., electronic or computer controller), for example by a servo screw, thereby potentially increasing flow rate accuracy and stability.

In yet other embodiments, the sample fluid pump 330 may be any other type of pump, including as representative examples not intended to be limiting, manual pumps, controller modulated pumps, or any other mechanisms that generate and sustain a constant or stable flow rate, such as gravitational pumps or vacuum pumps.

In some embodiments, the sample fluid pump 330 may include a sample preparation device to prepare the sample for injection into the evaporation cylinder 310. In some embodiments, the preparatory effect of a sample preparation device is to purify the sample. In such an embodiment, the sample preparation device may be any purifying modality, such as high performance chromatography (HPLC). In other embodiments, the preparatory effect of the sample preparation device is to separate the fluid sample into separate constituents which may be injected through the system in a time-resolved manner. In these embodiments, the sample preparation device may be any device capable of separating the sample into separate constituents in a time-resolved manner, including but not limited to phase extraction devices, liquid chromatographs, and electrophoretic devices. It should be understood that any sample preparation device may be used singly or in concert: if purity is desires, a purifying modality may be used; if time-gating is desired, a time-gating modality may be used; if purity and time-gating are desired, a purifying modality may be used, followed in sequence by a time-gating modality. Any appropriate sample preparation device may be used at this step.

In some embodiments, a carrier fluid may be used to provide a transfer medium for the constituents of the liquid sample fluid through the sample fluid pump 330 (and a sample preparation device if one is included), via liquid transfer system 130' to the evaporation cylinder 310. The carrier fluid may be incorporated into the sample prior to its insertion into the liquid REIMS system 300. Alternatively, the sample preparation device may provide for incorporation of the carrier fluid into the sample automatically. In embodiments where a sample preparation device provides for automatic incorporation of carrier fluid into the sample fluid, such a sample preparation device includes a reservoir of carrier fluid which it combines with the sample fluid in an appropriate carrier fluid to sample fluid ratio. Carrier fluid may be incorporated prior to sample preparation (and go through the sample preparation process with the sample fluid), or it may be incorporated after the sample preparation has been completed.

In some embodiments, the carrier fluid is composed of a single solvent or mixture of various solvents. The carrier fluid facilitates movement of the sample fluid from insertion into the sample fluid pump 330 to exiting the liquid transfer system 130' at the evaporation cylinder 310. In some embodiments, the carrier fluid has such advantageous properties that substantially full evaporation without the formation of significant solid residues is possible upon passing through the evaporation cylinder 310. Moreover, in some embodiments, the carrier fluid evaporates in the evaporation cylinder 310 at a rate greater than or equal to the rate of evaporation of the sample fluid.

In some embodiments, the evaporation cylinder control and power source 320 is electrically connected to the evaporation cylinder 310 and the evaporation cylinder control and power source 320 communicates in two-way communication with the evaporation cylinder 310. In other embodiments, the evaporation cylinder control and power source 320 is electrically connected to the evaporation cylinder 310 and the evaporation cylinder control and power source 320 communicates in only one-way communication with the evaporation cylinder 310. The evaporation cylinder control and power source 320 may serve to monitor the temperature of the evaporation cylinder 310 (e.g., via one or more temperature sensors on the evaporation cylinder 310) and keep it at a certain or predetermined temperature. Keeping the evaporation cylinder 310 at a constant temperature may be done through any of several methods, including but not limited to: using the material properties of the evaporation cylinder 310 and an empirical relationship between power applied to the material and heat generated; and including a temperature sensor which provides a feedback loop to the evaporation cylinder control and power source 320 and acts like a thermostat, such that the evaporation cylinder control and power source 320 may turn on when the temperature of the evaporation cylinder 310 has decreased to a certain level and may turn off when the temperature of the evaporation cylinder 310 has increased to a certain level.

In some embodiments, the evaporation cylinder control and power source 320 heats the evaporation cylinder 310 by providing alternating current to the evaporation cylinder 310 (e.g., to a heater attached to or incorporated in the evaporation cylinder 310). In other embodiments, the evaporation cylinder control and power source 320 heats the evaporation cylinder 310 by providing direct current to the evaporation cylinder 310 (e.g., to a heater incorporated in the evaporation cylinder 310).

In some embodiments, the evaporation cylinder control and power source 320 is controlled directly by the data analysis device 180'. In such embodiments, a user may program the evaporation cylinder control and power source 320 through the data analysis device 180', inputting such parameters such as length of heating and desired temperature.

In some embodiments, the evaporation cylinder 310 is fully cylindrical, meaning that there exists a solid cylinder for a full 360° with a central opening or channel therein. In other embodiments, the evaporation cylinder 310 may be partially cylindrical. In embodiments in which the evaporation cylinder 310 is only partially cylindrical, the partial cylinder of the evaporation cylinder 310 may be partial in the range of about 30° C.-800° C., about 40° C.-550° C., about 45° C.-<360° C., about 90° C.-<360° C., about 135° C.-<360° C., about 180° C.-<360° C., about 225° C.-<360° C., about 270° C.-<360° C., and including about 315° C.-<360° C.

In some embodiments, during operation, the evaporation cylinder 310 is kept between the boiling point and the Leidenfrost temperature of the sample fluid, thereby ensuring the most rapid evaporation possible. In some embodiments, during operation, the evaporation cylinder 310 is kept at a temperature substantially higher than the boiling point of the sample fluid but still under the sample fluid's Leidenfrost temperature.

In some embodiments, the evaporation cylinder 310 is constructed out of a high resistance material, capable of creating high temperatures upon application of electric power. Select examples of possible evaporation cylinder 310 materials, not intended to limit the scope of this disclosure, include the following: refractory metals, such as molybdenum, tantalum, tungsten, and nickel-iron; nickel-based alloys, such as nickel-chromium 35-19, nickel-chromium 68-20, nickel-chromium 60-16, nickel-chromium 80-20; iron based alloys, such as iron-aluminum, chromium-aluminum, molybdenum disilicide (including molybdenum doped with aluminum); or others, such as iron-nickel-chromium, aluminum-iron-chromium, Inconel, nickel-tungsten, cermets, silicon carbide, kanthal (FeCrAl), super kanthal, graphite, silicon carbide, ceramics, positive thermal coefficient of resistance ceramics, platinum. In some embodiments, an atmosphere other than air is used.

In some embodiments, the flow rate of the sample fluid in liquid state exiting the liquid transfer system 130' is low enough that substantially all of the sample fluid in liquid state 210 exiting the liquid transfer system 130' is vaporized as it hits, or substantially immediately after it hits, the cylindrical inner surface 312 of the evaporation cylinder 310. It may be undesirable for a residue of liquid in the form of a jet or droplets to remain unevaporated. In some embodiments, the embodiment of a liquid REIMS system 300 evaporates substantially all of the liquid sample (e.g., rate of evaporation is substantially equal to the flow rate out of the liquid transfer system 130'). In other embodiments, the embodiment of a liquid REIMS system 300 evaporates less than all of the liquid sample. The range of evaporation rates of the embodiment of a liquid REIMS system 300 are sufficient to convert one or more molecular components of the liquid sample to one or more gaseous ions. In some embodiments, the flow rate is in the range of about 10 nL/min-50 mL/min, about 100 nL/min-5 mL/min, about 1 µL/min-500 µL/min, and about 10 µL/min-50 µL/min including about 100 µL/min. In some embodiments the flow rate is high enough that the liquid sample fluid will not evaporate in the liquid transfer system 130' prior to reaching the cylindrical inner surface 312 of the evaporation cylinder 310. In some embodiments, the flow rate is optimized based on parameters of the embodiment of a liquid REIMS system 300 (e.g., evaporation cylinder 310 shape, size and surface characteristics, evaporation cylinder 310 temperature, sample fluid viscosity, sample fluid surface tension, etc) to advantageously address and evaporate substantially all of the sample fluid, thereby preventing sample loss. In some embodiments, the embodiment of a liquid REIMS system 300 evaporates only a portion of the sample thereby maintaining fluid flow over the electrodes during operation. The maintenance of constant flow when analyzing samples having high salt concentrations advantageously prevents the build-up of salts on the evaporation cylinder 310 surface.

The post ionization device 160' can be used to improve ion production after the conversion from liquid into gas the by evaporation cylinder 310 (and concomitant ion production by the evaporation cylinder 310). As shown in FIG. 3, the post ionization device 160' is an electrospray post ionization device which electrosprays pure solvent as multiply charged droplets directly through the lumen of the evaporation cylinder 310. The multiple charged droplets may merge with the aerosol particles of the sample fluid in its gaseous state thereby creating ionized species capable of being detected and analyzed by the ion analyzer device 170'.

In some embodiments, the post ionization device 160' may be any suitable ion source that can produce a sufficiently high current of ions. The ions created by the post ionization device 160' interact with the neutral particles produced by the evaporation cylinder 310 via electric charge transfer reactions thereby creating ionized species capable of being detected and analyzed by the ion analyzer device 170'. In other embodiments, the post ionization device 160' includes post-ionization by interaction with ionic species or metastable, electronically excited species originating from corona, glow or arc discharge.

In some embodiments, the liquid REIMS system 300 does not include a post ionization device 160'. Such embodiments are particularly feasible when the samples to be analyzed produce a high concentration of ionized species upon vaporization within the evaporation cylinder 310.

In some embodiments, the ion analyzer device 170' separately detects ions by using/detecting one or more of their chemically determined characteristics. In other embodiments, the ion analyzer device 170' separately detects ions by using/detecting one or more of their structurally determined characteristics. In yet other embodiments, the ion analyzer device 170' separately detects ions by using/detecting one of more of a combination of their chemically determined and structurally determined characteristics. For example, the ion analyzer device 170' may be a mass spectrometric analyzer which uses mass-to-charge ratio as its basis for separation. In another embodiment, the ion analyzer device 170' may be an ion mobility spectrometry analyzer which uses collisional cross section and charge. In some embodiments, other types of mass analyzers may be used, including, but not limited to any of the various ion trap instruments and time-of-flight analyzers. Ion trap instruments and time-of-flight analyzers may be used advantageously in embodiments in which the evaporation cylinder 310 produces a fluctuating ion current. The ion analyzer device 170' may generate data resulting from its analysis of the ions produced by the evaporation cylinder 310 or the evaporation cylinder 310 and post ionization device 160'. Generally, the data generated by the ion analyzer device 170' will be in the form of electronic data, processable by a computer.

In some embodiments, the evaporation cylinder 310 (or evaporation cylinder 310 and post ionization device 160' as the case may be) and ion analyzer device 170' are fully decoupled. In these embodiments, the liquid transfer system 130' delivers the sample fluid in liquid form to the evaporation cylinder 310 which converts it to its gaseous state which includes some number of ionic species. The gaseous sample may then be conveyed to the ion analyzer device 170' where it is analyzed. In such a decoupled system, any device, or combination of devices capable of delivering the gaseous sample ions from the evaporation cylinder 310 to the ion analyzer device 170' may be used.

In other embodiments, the evaporation cylinder 310 (or evaporation cylinder 310 and post ionization device 160' as the case may be) and ion analyzer device 170' are be fully coupled. In these embodiments, the liquid transfer system 130' delivers the sample fluid in liquid form to the evaporation cylinder 310 which converts it to its gaseous state which includes some number of ionic species. Because the evaporation cylinder 310 and ion analyzer device 170' are coupled in these embodiments, the gaseous sample may be directly read/analyzed by the ion analyzer device 170' without the need for any of the aforementioned transportation required by a fully decoupled system.

In some embodiments, the data analysis device 180' is a computer and appropriate analysis software. In these embodiments, the data analysis device 180' converts the raw electronic signal generated by the ion analyzer device 170' into analytical information. In some embodiments, the data analysis device 180' includes a device by which the analytical information may be conveyed to a user. In some embodiments, information may be conveyed in the form of full spectra on a screen or in print-outs. In other embodiments, when only a positive/negative response is desired (such as in urine drug testing) information may be conveyed in a binary format, such as by an aural tone for positive, a simple positive/negative result visually displayed on a monitor or printout, etc. Any of a number of reporting methods may be used depending on the application for the liquid REIMS system 300.

Figure 4:
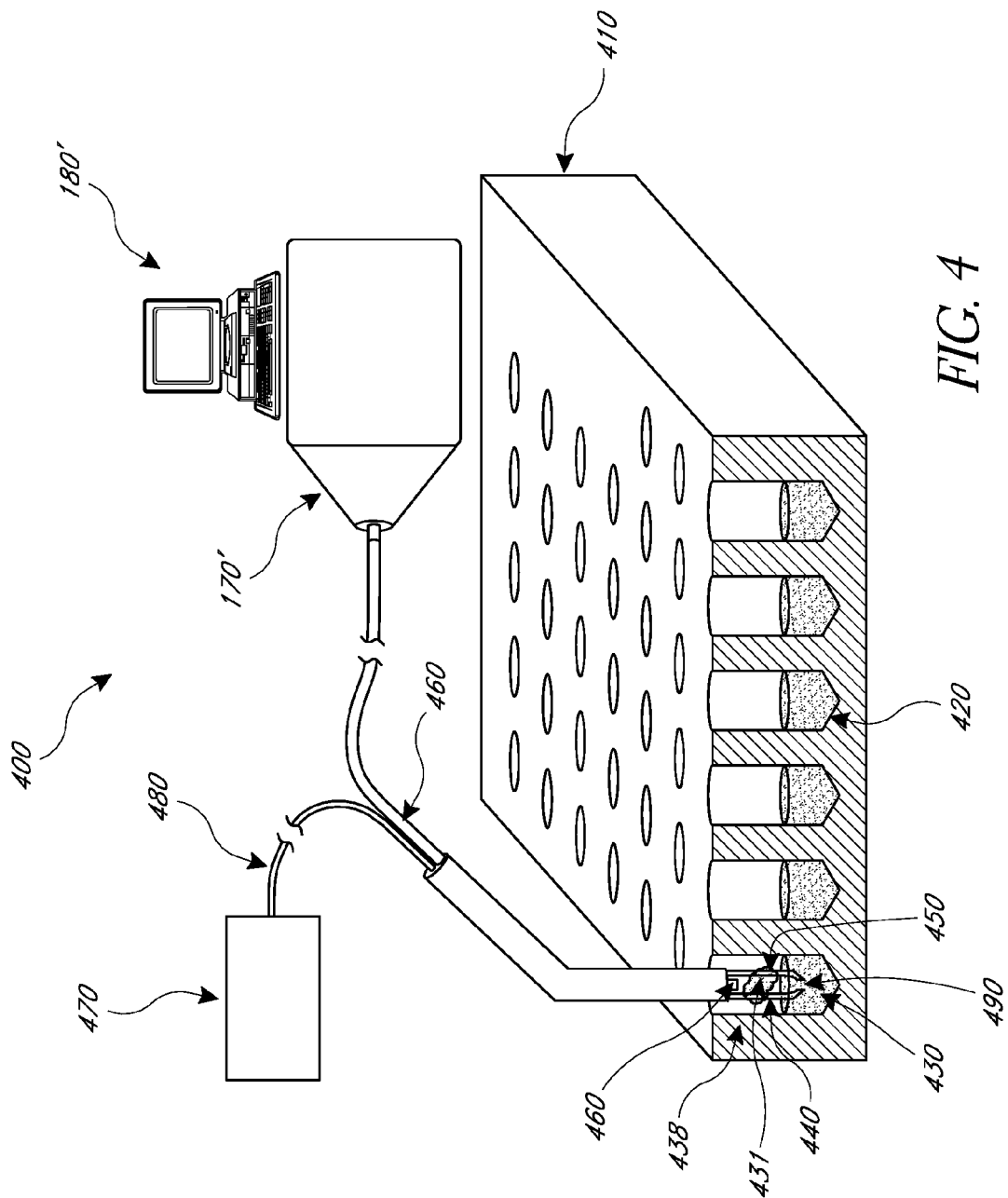
FIG. 4 is a schematic view of still another embodiment of a system for converting a liquid phase sample into gaseous ions and for analyzing the gaseous ions.

FIG. 4 illustrates another embodiment of a liquid REIMS system 400. The liquid REIMS system 400 includes a microtiter plate 410, at least one microwell 420 which can be filled with a sample fluid in its liquid state 430, a sample fluid in its gaseous state 431 generated by the liquid REIMS system 400, a thermal evaporation ionizing device 438 with a first electrode 440 and a second electrode 450, a gaseous sample transport conduit 460, an electrode power source 470, an electrode lead line 480, an electrode bridge gap 490, an ion analyzer device 170', and a data analysis device 180'.

In the liquid REIMS system 400, the sample fluid in its liquid state 430 and second electrode 450 are positioned and fixed such that a fixed electrode bridge gap 490 is created between the tip of the first electrode 440 and the second electrode 450. The electrode power source 470 is connected to the first electrode 440 and second electrode 450 via of the electrode lead line 480. The gaseous sample transport conduit 460 runs from just above the electrode bridge gap 490 created by the first electrode 440 and second electrode 450 to the ion analyzer device 170'. The data analysis device 180' can be in data communication with the ion analyzer device 170'. The microtiter plate 410 includes at least one microwell 420 which may contain sample fluid in its liquid state 430.

In operation, sample fluid in its liquid state 430 is placed (e.g., injected) into at least one of the microwells 420 of the microtiter plate 410. The first electrode 440 and second electrode 450 are then at least partially submerged in the sample fluid in its liquid state 430. The electrode power source 470 then creates a potential difference across the first electrode 440 and second electrode 450 through the electrode lead line 480. In some embodiments, the first electrode 214 is a negative electrode and the second electrode 216 is a positive electrode. In other embodiments, the first electrode 214 is a positive electrode and the second electrode 216 is a negative electrode. The sample fluid in its liquid state 430 in the electrode bridge gap 490 completes the circuit between the first electrode 440 and second electrode 450. The power created in the electrode bridge gap 490 vaporizes at least some of the sample fluid in its liquid state 430, thereby creating sample fluid in its gaseous state 431. The sample fluid in its gaseous state 431 includes at least some concentration of ionic species (e.g., including gaseous ions). Sample fluid in its gaseous state 431 is taken up by the gaseous sample transport conduit 460 to the ion analyzer device 170' where it is read/analyzed. The ion analyzer device 170' can communicate the raw data to the data analysis device 180' where it is analyzed and communicated to a user. In some embodiments data is transmitted from the ion analyzer device 170' automatically to the data analysis device 180'. In other embodiments data is written to removable memory at the ion analyzer device 170' and can be removed from the ion analyzer device 170' and read, analyzed and used by and at the data analysis device 180'. Removable memory includes any form of computer readable media which can be transferred from one data reading or writing device to another data ready or writing device, including but not limited to: floppy disks, zip disks, compact disks (i.e., CDs), digital video disks (i.e., DVDs), BlueRay® disks, HD DVD disks, holographic disks, plate-based hard drives, solid state hard drives, and any type of flash memory. In another embodiment, data is communicated wirelessly (e.g., using radiofrequency communication) from the ion analyzer device 170' to one or more data analysis device 180'.

In some embodiments, the microtiter plate 410 is a standard 96 well plate. It may be undesirable that samples mix, even sample residues. In some embodiments, 96 well plates may be used advantageously in that they are ideally adapted to single use applications—one microwell 420 may be used to read one sample until all microwells 420 in a plate have been used then the plate may be discarded. In other embodiments, the microtiter plate 410 is a reusable plate. The microtiter plate 410 may be any construct having at least one microwell 420 capable of holding some sample fluid in its liquid state 430 and capable of accepting the first electrode 440 and second electrode 450.

In some embodiments, the first electrode 440 and second electrode 450 have sharp tips, thereby improving the focusing of electric current. In some embodiments, the first electrode 440 and second electrode 450 have blunted, or rounded tips. In other embodiments, the first electrode 440 and second electrode 450 have square tips.

In some embodiments, the electrode bridge gap 490 between the first electrode 440 and second electrode 450 is in the range of about 0.1 mm-5 mm, about 0.2-2.5 mm, about 0.3-1.5 mm, and about 0.4-0.75 mm, about 0.5-0.6 mm including about 1 mm.

In some embodiments, the electrode power source 470 creates an electrical potential difference across the first electrode 440 and second electrode 450. In these embodiments, as mentioned above, if any type of carrier liquid or sample preparation fluid is used, it may be highly advantageous that the carrier liquid or sample preparation fluid be electrically conductive (such as an aqueous solvent system), to thereby facilitate completion of the electrical circuit between the first electrode 440 and second electrode 450. In some embodiments, the potential is 300 Vp-p, 330 Hz alternating electrical potential.

In some embodiments, the potential difference applied to the first electrode 440 and second electrode 450 is a direct potential difference. In other embodiments, the potential difference applied to the first electrode 440 and the second electrode 450 is an alternating potential difference. In some embodiments, the magnitude of the potential difference applied across the first electrode 440 and the second electrode 450 is in the range of about 10V/mm-100 kV/mm, about 50v/mm-20 kV/mm, about 250v/mm-4 kV/mm, about method for analyzing a liquid sample using liquid rapid evaporative ionization of liquid phase samples 500V/mm-2 kV/mm, and about 750V/mm-1 kV/mm. In some embodiments, the highest voltage possible without discharge through the air is used to advantageously thermally evaporate the liquid sample.

In some embodiments, the electrode power source 470 is capable of detecting resistance between the first electrode 440 and second electrode 450. In such embodiments the electrode power source 470 responds differently to different levels of resistance: the electrode power source 470 may maintain a low level potential difference (resting power) across the first electrode 440 and second electrode 450 as long as the electrode power source 470 detects that there exists a substantially high resistance between the first electrode 440 and 450 (corresponding to the presence of air between the electrodes); the electrode power source 470 may increase to a high potential difference (vaporizing power) across the first electrode 440 and second electrode 450 when the electrode power source 470 detects that there is a substantially low resistance between the first electrode 440 and second electrode 450 (corresponding to the presence of a conductive sample between the electrodes). In such embodiments, the electrode power source 470 may turn off when the first electrode 440 and second electrode 450 are removed from a sample, and the electrode power source 470 may turn back on when the first electrode 440 and second electrode 450 are once again submerged in a conductive sample. This would have the advantageous effect of acting as a feedback loop, turning off the electrode power source 470 once the first electrode 440 and second electrode 450 have completely vaporized a sample.

In some embodiments, the electrode lead line 480 connects the electrode power source 470 to the first electrode 440 and second electrode 450 and is constructed out of any type of conductive, flexible material, such as traditional copper wiring.

In some embodiments, the gaseous sample transport conduit 460 begins above the electrode bridge gap 490 in the range of about 0.5-10 mm above the electrode bridge gap 490, about 0.6-8 mm above the electrode bridge gap 490, 0.7-6 mm above the electrode bridge gap 490, 0.8-4 mm above the electrode bridge gap 490, 0.9-2 mm above the electrode bridge gap 490, and including 1 mm above the electrode bridge gap 490. In some embodiments, the gaseous sample transport conduit 460 is a flexible, hollow tubular structure with a lumen extending from the proximal end of the gaseous sample transport conduit 460 (beginning above the electrode bridge gap 490) to the distal end of the gaseous sample transport conduit 460 which terminates at the ion analyzer device 170'. In some embodiments, the gaseous sample transport conduit 460 has an internal lumen diameter in the range of about 0.5-5 mm, about 0.75-2.5 mm, and about 1-2 mm, including about 1.5 mm. In some embodiments, as small an internal lumen diameter as possible is used to advantageously aid in detection speed.

In some embodiments, the gaseous sample transport conduit 460 is constructed out of any appropriate plastic, such as polyetheretherketone (PEEK) or polytetrafluoroethylene (PTFE).

In some embodiments of the liquid REIMS system 400, an injector device is used to aid in the transport of the sample fluid in its gaseous state 431 from the proximal end of the gaseous sample transport conduit 460 to the distal end of the gaseous sample transport conduit 460 and the ion analyzer device 170'. Such an injector device may be advantageous to provide for a carefully modulated injection of the sample fluid in its gaseous state 431 to the ion analyzer device 170'. The injector device may be a loop injector as is used in several commercial devices.

Additionally, in some embodiments of the third embodiment of a system for liquid REIMS 400, it may be advantageous to include a post ionization device to further ionize the sample fluid in its gaseous state 431. This may be particularly advantageous when the sample fluid in its liquid state 430 is one that upon conversion to sample fluid in its gaseous state 431 does not create a high concentration of ions.

In some embodiments of the liquid REIMS system 400, the system may be semi-automated. For example, a user may load a 96 well plate, or microtiter plate 410, with the desired samples and then use the data analysis device 180' (essentially a computer) to indicate which wells of the 96 well plate are filled with sample fluid in its liquid state 430. The 96 well plate may then be placed on a stage, preprogrammed to be articulable along the X and Y axes of the Cartesian plane. Therefore, the 96 well plate may easily be move, one microwell 420 at a time to the left and right or up and down. In this example, the electrode assembly, comprised of the first electrode 440, second electrode 450 and electrode lead line 480 and gaseous sample transport conduit 460 is placed vertically above the articulating 96 well plate stage. The electrode assembly may move up and down in the Z direction while remaining stationary in X and Y. The data analysis device 180' may communicate sample locations to the electrode assembly, causing the electrode assembly to drop and activate to vaporize as disclosed above. In operation then, a user may load a plate with samples, indicate to the data analysis device 180' which microwells 420 contain samples, place the plate on the articulable stage and activate the system. Once activated, the system may automatically translate the stage to the first filled microwell 420, drop the electrode assembly into the sample and analyze the sample as discussed above. The system may then retract the electrode assembly, translate the stage to the next filled microwell 420, and then repeat the process until all filled microwells 420 in the plate have been analyzed.

In some embodiments, the aforementioned automation may be effected by incorporating all three X/Y/Z translation into the electrode assembly, as opposed to giving the stage X/Y translation and giving the electrode assembly Z translation.

Figure 5:
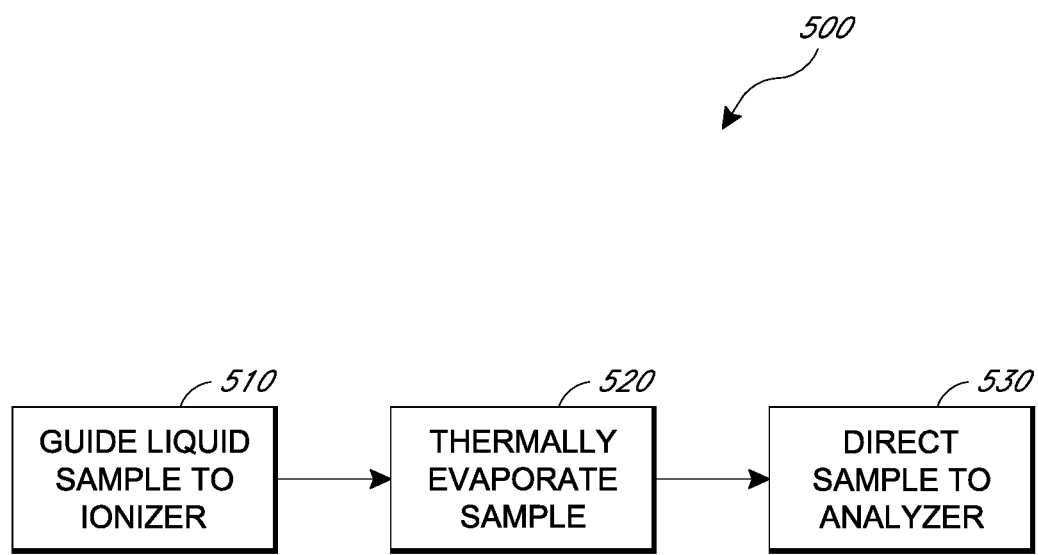
FIG. 5 is a flow chart of one embodiment of a method for converting a liquid phase sample into gaseous ions and for analyzing the gaseous ions.

FIG. 5 illustrates a method for analyzing a liquid sample using liquid rapid evaporative ionization of liquid phase samples 500.

First at step 510, a liquid sample is guided to a thermal evaporation ionizing device 150'.

In some embodiments, the liquid sample is guided to the thermal evaporation ionizing device 150' through a liquid transfer system 130'. In some embodiments, the liquid sample is conveyed along the liquid transfer system 130' via a pump which may be any of a number of different types of pumps, including representatively, syringe pumps, membrane pumps, piston pumps, electrokinetic pumps, pumps employing Venturi's principle, manual pumps, controller modulated pumps, or any other mechanism that generates and sustains a constant or stable flow rate, such as gravitational pumps or vacuum pumps.

Next at step 520, the liquid sample is thermally evaporated by the thermal evaporation ionizing device. In some embodiments, the thermal evaporation ionizing device is the thermal evaporation ionizing device 150 shown in FIG. 1. In some embodiments, the thermal evaporation ionizing device is the thermal evaporation ionizing device 200 shown in FIG. 2A. In some embodiments, the thermal evaporation ionizing device is the thermal evaporation ionizing device 201 shown in FIG. 2B. In other embodiments, the thermal evaporation ionizing device is the thermal evaporation ionizing device 202 shown in FIG. 2C. In yet other embodiments, the thermal evaporation ionizing device is the thermal evaporation ionizing device 310 shown in FIG. 3. In still other embodiments, the thermal evaporation ionizing device is the thermal evaporation ionizing device 438 shown in FIG. 4.

Next at step 530, the sample in its gaseous state is directed to a sample analyzer where is it analyzed (e.g., to obtain or provide information on the chemical composition of the liquid sample).

Figure 6:
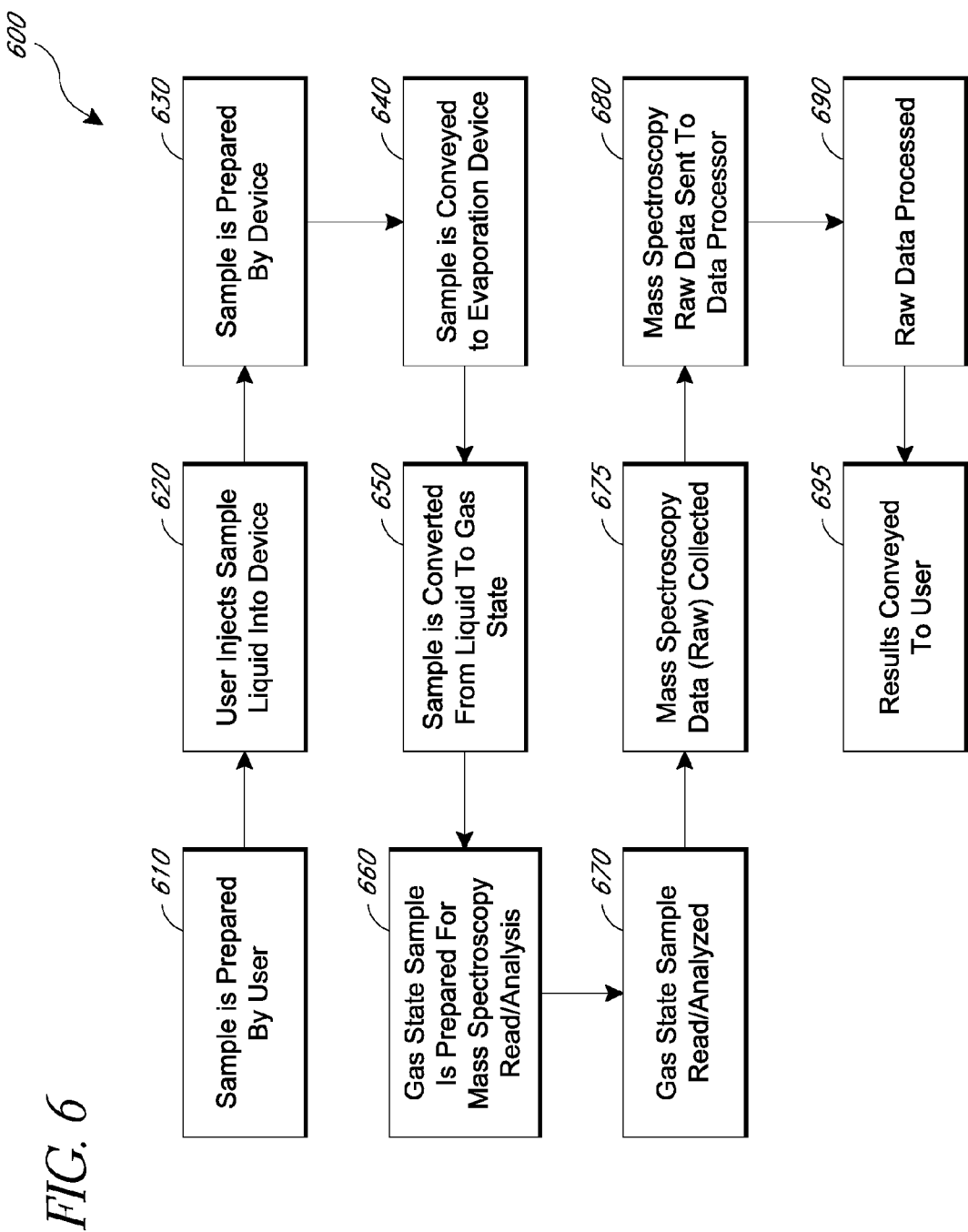
FIG. 6 is a flow chart of another embodiment of a method for converting a liquid phase sample into gaseous ions and for analyzing the gaseous ions.

FIG. 6 illustrates another flow chart of a method for analyzing a liquid sample using liquid rapid evaporative ionization of liquid phase samples 600.

First, at step 610, a liquid sample fluid to be analyzed is prepared by a user.

In some embodiments, step 610 may include filtration, HPLC, separation, precipitation, or any other sample preparation method which may be helpful. In some embodiments, step 610 may include mixing the sample of interest with a carrier fluid to facilitate movement through the system.

In some embodiments, there is no preparation by the user (i.e., step 610 is excluded).

Next, at step 620, the user injects the liquid sample fluid into the system for liquid rapid evaporative ionization mass spectrometry (embodiments of which are illustrated in FIGS. 1, 3, and 4).

In some embodiments, the liquid sample fluid injected by the user is a prepared sample (such as filtered, precipitated, etc.). In some embodiments, the liquid sample fluid injected by the user is a combination of sample of interest and carrier fluid.

In some embodiments, the injection may be accomplished by physically injecting the liquid sample fluid into the system, for example by coupling a syringe filled with some volume of liquid sample fluid and depressing the syringe's plunger thereby causing the fluid to be forcefully injected into the system. In other embodiments, other forms of entry may be used, for example pouring, pipetting, vacuum, etc.

Next, at step 630, the liquid sample fluid is prepared by the system for liquid rapid evaporative ionization mass spectrometry for subsequent rapid evaporation and mass spectrometry analysis.

In some embodiments, the liquid sample fluid preparation effected by the system may include one or more of the following: incorporation of carrier fluid, purification (such as by HPLC), and individual constituent time-resolved eluting (such as by phase extraction devices, liquid chromatographs, and electrophoretic devices).

In some embodiments, the system does not prepare the liquid fluid sample in any manner (i.e., step 630 is excluded).

Next, at step 640, the liquid sample fluid is conveyed to the rapid evaporation device.

In some embodiments, the liquid sample fluid is conveyed along the liquid transfer system 130 via a liquid pump and or an injector device 120. In some embodiments, such devices may be advantageously used to allow an evenly metered or evenly variable flow rate. In other embodiments, the liquid sample fluid is conveyed along the liquid transfer system 130 in other ways such as gravity or a pressure differential (such as application of a vacuum).

Next, at step 650, the liquid sample fluid is converted via thermal evaporation by the thermal evaporation ionizing device 150 into a gas sample fluid which contains some concentration of ionized species.

In some embodiments, the thermal evaporation ionizing device 150 is a pair of electrodes (as illustrated in FIGS. 2A and 4), a hot surface (as illustrated in FIGS. 2B and 3), or at least one beam of electromagnetic radiation (as illustrated in FIG. 2C).

Next, at step 660, the gas sample fluid is prepared for mass spectroscopic analysis.

In some embodiments in which a high (or higher) concentration of ionic species is desired, the gas sample fluid is prepared by using a post ionization device 160 (e.g., secondary ion source). In some embodiments, the post ionization device 160 may be an electrospray ion source. In other embodiments, the post ionization device 160 may cause post-ionization by interaction with ionic species or metastable, electronically excited species originating from corona, glow or arc discharge.

In some embodiments, there is no post-evaporative gas sample fluid preparation (e.g., step 660 is excluded).

Next, at step 670, the prepared gas sample fluid is read/analyzed by the ion analyzer device 170.

In some embodiments, the ion analyzer device 170 separately detects ions by using/detecting one or more of their chemically determined characteristics. In other embodiments, the ion analyzer device 170 separately detects ions by using/detecting one or more of their structurally determined characteristics. In yet other embodiments, the ion analyzer device 170 separately detects ions by using/detecting one of more of a combination of their chemically determined and structurally determined characteristics. For example, the ion analyzer device 170 may be a mass spectrometric analyzer which uses mass-to-charge ratio as its basis for separation. Alternatively, the ion analyzer device 170 may be an ion mobility spectrometry analyzer which uses collisional cross section and charge. In some embodiments, other types of mass analyzers may be used, including, but not limited to any of the various ion trap instruments and time-of-flight analyzers.

Next, at step 675, the ion analyzer device 170 collects raw mass spectrometry data.

In some embodiments, the raw mass spectrometry data will be in the form of time-of-flight data. In other embodiments, the raw mass spectrometry data will be mass-to-charge ratio data. In yet other embodiments, the raw mass spectrometry data will be collisional cross section and charge data.

Next at step 680, the ion analyzer device 170 communicates the raw mass spectrometry data from the ion analyzer device 170 to the data analysis device 180.

In some embodiments, the data analysis device 180 is a computer in data communication with the ion analyzer device 170.

Next at step 690, the data analysis device 180 processes the raw mass spectrometry data received from the ion analyzer device 170, converting it from raw mass spectrometry data to processed mass spectrometry data.

Next at step 695, the data analysis device 180 conveys the processed mass spectrometry data to the user.

In some embodiments, the data analysis device 180' includes a device by which the analytical information may be conveyed to a user. In some embodiments, information may be conveyed in the form of full spectra on a screen or in print-outs (for example print-out created by a printer connected to the data analysis device 180). In other embodiments, when only a positive/negative response is desired (such as in urine drug testing) information may be conveyed in a binary format, such as by an aural tone for positive, a simple positive/negative result displayed on a monitor or printout, etc. Any of a number of reporting methods may be used depending on the application.

ILLUSTRATIVE EXAMPLES

Example 1

Quantitative Determination of Constituents of Biological Samples by Liquid Chromatographic Separation Followed by Evaporative Ionization Mass Spectrometry (LREIMS)

Concentrations of biological sample constituents may be determined by using high performance liquid chromatographic (HPLC) mass spectrometric methods. Biological samples are generally prepared for analysis through liquid/liquid extraction, solid phase extraction, precipitation of proteins by organic solvents or any other of a number of appropriate sample preparation methods used in analytical chemistry.

In the case of protein precipitation by organic solvents, an organic solvent (such as acetonitrile, methanol, or any other solvent which is at least partially miscible with water) is added to the biological sample resulting in the precipitation of proteins. Precipitate proteins may then be removed through centrifugation or filtration. Depending on the sample composition, it may be necessary to adjust the sample's solvent composition or pH. Such adjustment may be effected by adding solvents or buffer solution. Alternatively, the sample may be completely dehydrated/evaporated (thereby removing all solvent and aqueous species) then reconstituted using only the appropriate and desired solvent system.

The sample can be subjected to HPLC analysis by injecting the appropriate volume of the sample into an HPLC column. Typically, a reverse phase, octadecyl-silica packing is used, generally with the following properties: 1-5 µm particle size, 10-250 mm column length, and 1-4.6 mm column diameter. Constituents of the injected sample are eluted using either constant composition of a carrier fluid (constant carrier fluid concentration—known commonly as isocratic elution), or by changing composition of a carrier fluid (changing carrier fluid concentration—known commonly as gradient elution). In this example, the carrier fluid is electrically conductive.

The system as described is advantageously compatible with traditional buffer system (such as potassium or sodium phosphate buffers) or any carrier liquid containing high concentrations of organic or inorganic salts.

After HPLC, if HPLC is desired, the constituents of the biological sample carried by the carrier liquid through the fluid system are introduced into an ionizing device.

In this example, the ionizing device is comprised of two cylindrical electrodes, each having a diameter of 5 mm (or a surface area of approximately 78.540 $mm^2$) the surfaces of which are held at a fixed distance of 1 mm away from each other. The surfaces of the electrodes are roughened mechanically or electrochemically in order to obtain a high specific surface area. The system used in this example is an embodiment of that disclosed herein in FIGS. 1 and 2A.

Carrier liquid carrying the constituents of the biological samples (created in the aforementioned steps) is introduced between the two electrodes of the evaporative ionizing device. Direct or alternating current electric potential is applied between the two electrodes. Such current may be applied either continuously or intermittently.

In the case of continuous application of electric potential difference between the two electrodes, the electrically conductive carrier liquid closes or completes the electric circuit thereby resulting in electric current flowing rapidly through the carrier liquid/sample present between the two electrodes. The high electric current rapidly increases the temperature of the carrier liquid/sample to boiling thereby resulting in evaporation of substantially all of the carrier liquid/sample. This example used electric power values in the order of approximately 10-100 W to see the desired evaporation performance.

In the case of intermittent application of electric potential difference between the two electrodes, accumulation of carrier liquid between the electrodes may be monitored by measuring the resistance between the two electrodes—as the gap is filled by the electrically conductive sample, the resistance decreases. Electric potential for evaporation may be applied to the electrodes when the appropriate amount of carrier liquid is present between the electrode surfaces. Intermittent or discontinuous application of electric current may render evaporation of the carrier liquid more reproducible that continuous application of electrical potential difference. In the cases of intermittent application of electric current, the duty cycle of the ion analyzer may be synchronized with the application of electric current and therefore the production of ions.

As the carrier liquid is evaporated, the components of the biological fluid sample are transferred to their gas phase in both ionic and neutral forms. This formation of fully desolvated ions takes place easily at atmospheric pressures. Alternatively, it may be done inside the sub-atmospheric pressures required by the ion analyzer device.

Ion species entering the ion analyzer are separately detected based on their different mass-to-charge ratio or their different mobility (as is known, mass spectrometers are used for mass-to-charge ratio based separation and detection while ion mobility spectrometers are used for mobility-based separation and detection). A combination of both mass spectrometry and ion mobility spectrometry may also be used when multiple components of biological samples undergo ionization.

The intensity of ionic species detected by the ion analyzer(s) corresponding to components of the original biological fluid sample is then used to extract information about those components' concentrations in the original biological fluid sample.

Example 2

Qualitative, Semi-Quantitative Determination of Toxins in Urine by Evaporative Ionization Mass Spectrometry (LREIMS)

Qualitative/semi-quantitative determination of toxic compounds in urine is a critical step in the differential diagnosis of poisoning cases at emergency rooms. Since therapy options and choices are largely dependent on the type of toxin implicated, qualitative determination of toxins is required in all such cases. Furthermore, it is crucial that the urinalysis time demand be minimized.

Here, a syringe is filled with 1 ml of fresh urine and placed into a syringe pump. A fluid transfer system (consisting of a 1.588 mm outer diameter, 1.27 mm inner diameter polytetrafluoroethylene (PTFE) tubing and appropriate connecting elements) is used to connect the syringe pump to an evaporative ionizing device.

In this case, the evaporative ionizing device consists of a hollow ceramic cylinder (12.7 mm internal diameter and 25.4 mm long) equipped with external resistance heating. The evaporative ionizing device used in this case is capable of being heated to between 150° C. and 800° C. The system used in this example is an embodiment of that disclosed herein in FIG. 3. The fluid transfer system terminated in the interior lumen of the ceramic cylinder evaporative ionizing device.

The syringe pump pumps the urine through the fluid transfer system and out onto the pre-heated ceramic surface. Constituents of the urine sample are converted to gaseous ions and gaseous neutrals upon the rapid thermal evaporation of the sample. The gaseous neutrals are ionized using an electrospray source (spraying typically 1-100 μL methanol/water solvent solution in a 1:1 ratio) spraying through the heated ceramic tubing. Electrosprayed charged droplets pick up neutrals formed on the thermal evaporation of the liquid urine sample. Charged droplets containing the relevant toxic constituents of the urine sample are evaporated in either the heated ceramic tubing or in the sub-atmospheric pressure regime of the ion analyzer.

Gaseous ions corresponding to the toxic constituents of the urine sample are analyzed by mass spectrometry (based on the different mass-to-charge ratio of ionic species). Note, ion mobility spectrometry could also be used (basing its results on the different gas phase mobility of ionic species). Ionic species separated by mass spectrometry could also advantageously be subjected to tandem mass spectrometric analysis and identified based on their fragmentation patterns.

Example 3

Diagnosis of Inborn Errors of Metabolism by the Direct Evaporative Ionization Mass Spectrometric Analysis of Urine Samples Congenital metabolic errors are frequently screened at the population level in developed countries. Currently used screening methods however do not provide sufficiently detailed information to establish a solid diagnosis and start appropriate therapy. Therefore, patients identified to possess such metabolic errors usually under further confirmatory diagnostic testing, comprising the detailed analysis of various bodily fluids with special emphasis on urine. Analysis of urine samples has traditionally been performed by gas chromatography-mass spectrometry (GC-MS) methods, following chemical derivatization of the samples. While GC-MS is highly sensitive, it is time consuming and expensive. The method disclosed herein, used in the following example can reduce the time demand of analysis from several hours (including sample preparation) to simply a few seconds.

100 μl aliquots of urine were pipetted into round-bottom 96 well microtiter plates. A pair of needle electrodes was introduced into PTFE tubing (with 3.175 mm outer diameter and 2.0 mm inner diameter) such that the two electrodes extended from the proximal end of the tubing. The distal end of the tubing was directly connected to a high resolution mass spectrometer.

The electrode tips were immersed into the urine samples (individually) 300 $V_{p-p}$, 330 Hz alternating electrical potential was applied to the electrodes for three seconds. The aerosol formed on the thermal evaporation of the urine sample was directly introduced into the atmospheric interface of the high resolution mass spectrometer. The system used in this example is an embodiment of that disclosed herein in FIG. 4.

The high resolution mass spectrometer was able to detect positive molecular ions of medium chain acyl-carnitines in positive ion mode. Positive molecular ions of medium chain acyl-carnitines are a marker produced by patients suffering from medium chain acyl-coenzyme A dehydrogenase deficiency. The high resolution mass spectrometer was also able to detect various dicarboxylic acids and acyl-glycines in negative ion mode.

Figure 7:
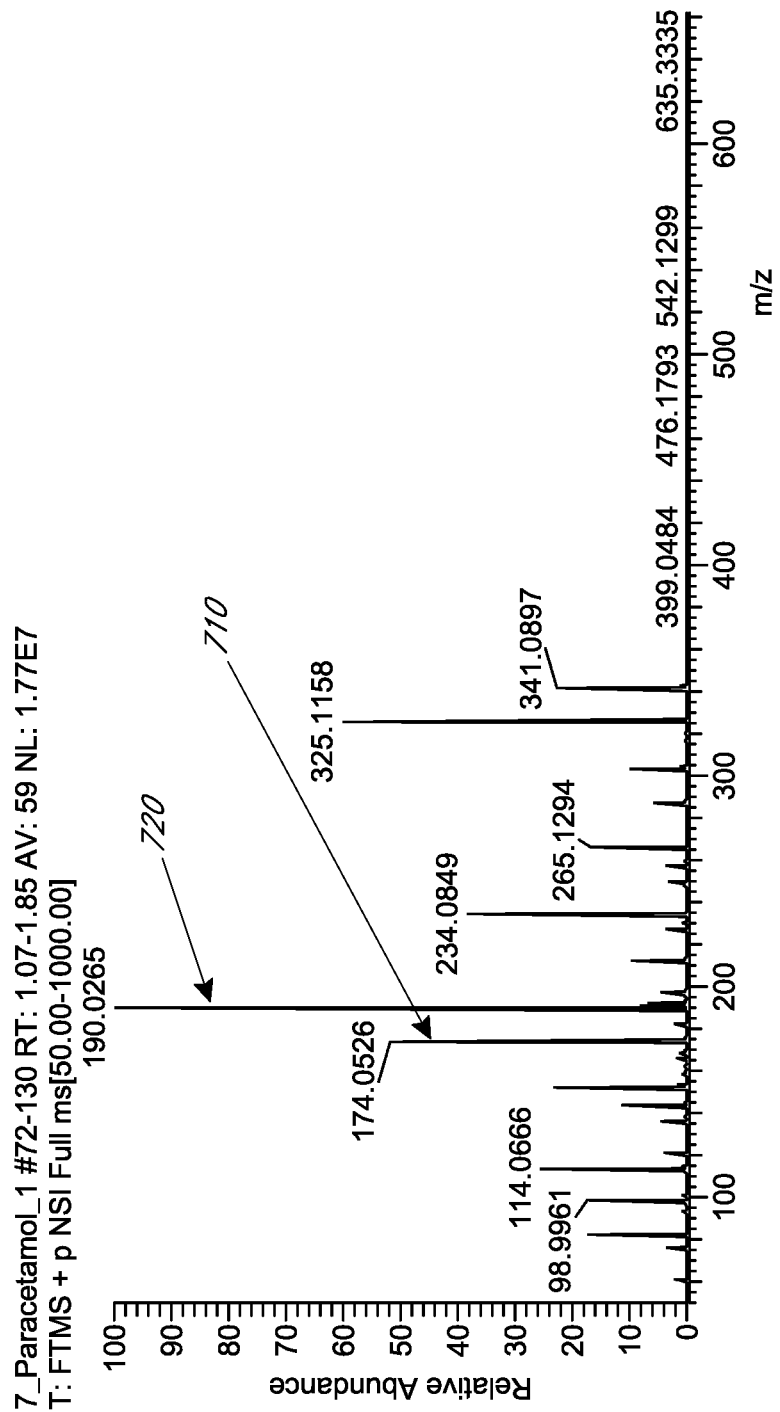
FIG. 7 is a graph of a spectrum for a liquid sample produced using the system of FIG. 4.

FIG. 7 illustrates a spectrum produced using an embodiment of the system disclosed in FIG. 4. The mass spectrum was obtained from a urine sample analyzed 8 hours after the ingestion of 100 mg of paracetamol. Peak 1 710 corresponds to the sodiated molecular ion of the drug. Peak 2 720 corresponds to the potassiated molecular ion of the drug. FIG. 7 demonstrates that this system may be used as an accurate and effective mechanism for liquid mass spectrometry.

Figure 8A:
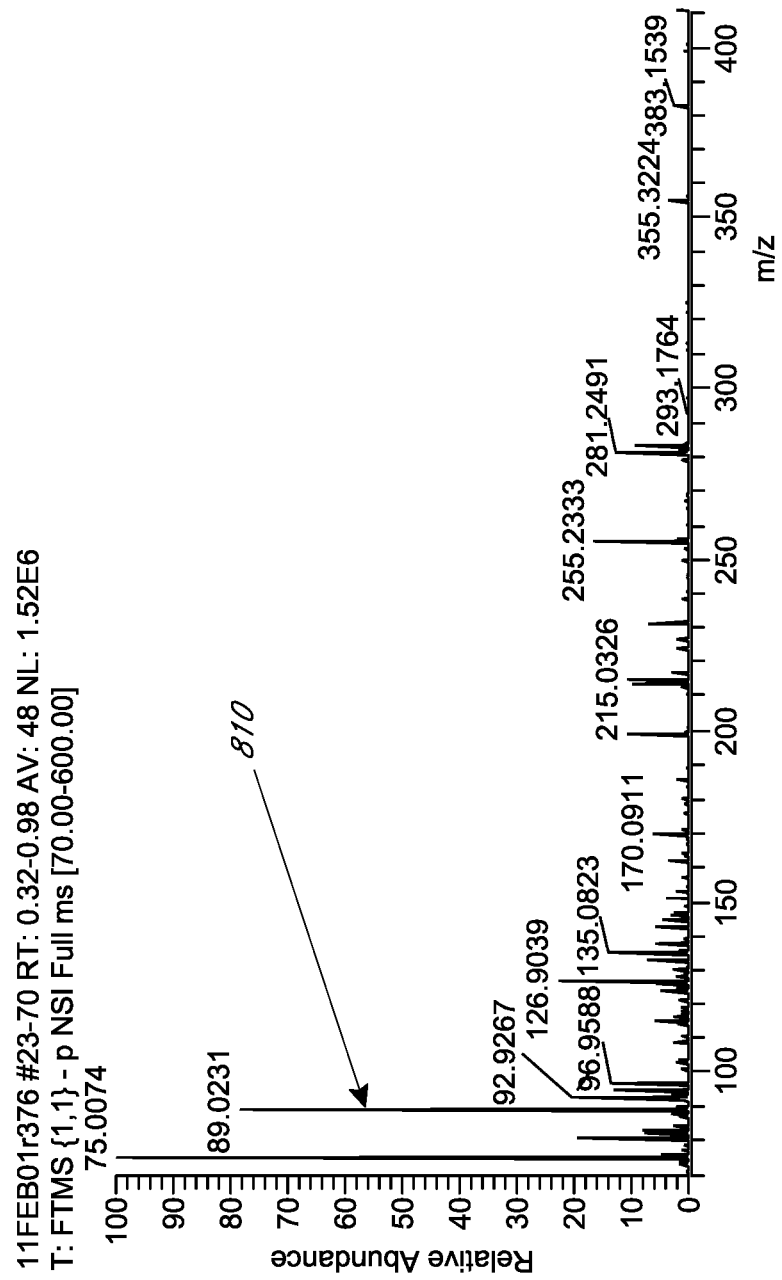
FIGS. 8A and 8B are spectra from separate urinalyses produced using the system of FIG. 4.
Figure 8B:
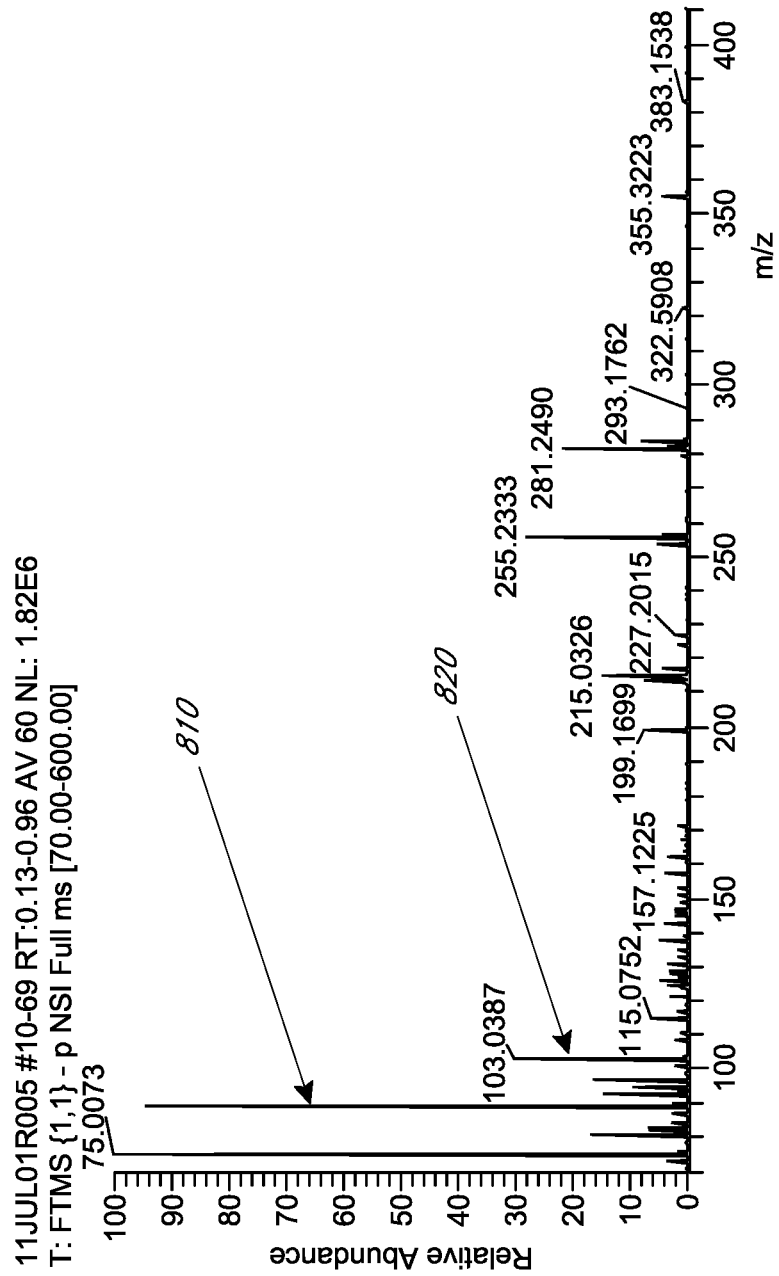

FIG. 8 illustrates spectra from separate urinalyses obtained using an embodiment of the system disclosed in FIG. 4. FIG. 8A illustrates the urinalysis spectrum obtained from a healthy individual while FIG. 8B illustrates the urinalysis spectrum obtained (in negative ion mode) from an individual suffering from medium chain acyl-CoA dehydrogenase deficiency (MCADD). As can be seen from the spectra, peak 1 810 in FIG. 8B is significantly higher than peak 1 810 in FIG. 8A. Furthermore, peak 2 820 in FIG. 8B is not present in FIG. 8A. Both of these abnormal peaks are indicators of MCADD. Therefore, FIG. 8 establishes that this system may be used as an accurate and effective mechanism for detecting MCADD simply through urinalysis.

The liquid REIMS systems 100, 200, 300, 400 and thermal evaporation ionizing devices 150, 200, 201, 202, 310, 438 disclosed herein have several advantages over currently available systems which render its use highly advantageous in many scenarios. The system disclosed provides for a very easy mass-spectrometric or ion-mobility spectrometric analysis of fluid samples while eliminating the problem of clogging due to the presence of solid, floating material experienced by spray ionization. Additionally the system disclosed herein eliminates problems created by widely varying sample viscosities, high concentrations of either organic or inorganic salts in fluid samples (such as phosphate buffers or sodium chloride), and high degrees of chemical complexity. Moreover, liquid REIMS is particularly well suited to the addition of a secondary ionization source, does not require expensive and sophisticated high-pressure hardware, is compatible with solid phase REIMS systems, permits very rapid sample preparation, and lastly is highly robust.

Of course, the foregoing description is of certain features, aspects and advantages of the present invention, to which various changes and modifications can be made without departing from the spirit and scope of the present invention. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of the specific features and aspects between and among the different embodiments may be made and still fall within the scope of the invention. Accordingly, it should be understood that various features and aspects of the disclosed embodiments can be combined with or substituted for one another in order to form varying modes of the discussed devices, systems and methods (e.g., by excluding features or steps from certain embodiments, or adding features or steps from one embodiment of a system or method to another embodiment of a system or method).

What is claimed is:

1. A method for analyzing liquid phase samples, comprising generating a sample aerosol from a liquid sample;

transporting the sample aerosol to an analyzer device;
introducing the sample aerosol into a sub-atmospheric pressure regime of the ion analyzer device;

desolvating the sample aerosol in the sub-atmospheric pressure regime of the ion analyzer device to produce sample ions.

2. The method of claim 1, wherein generating a sample aerosol comprises thermally evaporating the liquid sample.

3. The method of claim 2, wherein thermally evaporating the liquid sample comprises applying an electric current to the liquid sample through a gap between a pair of electrodes.

4. The method of claim 2, wherein thermally evaporating the liquid sample comprises heating the sample using at least one electromagnetic radiation beam.

5. The method of claim 4, wherein the at least one electromagnetic radiation beam comprises a laser.

6. The method of claim 1, wherein thermally evaporating the liquid sample comprises applying an electric current to the liquid sample between a pair of electrodes.

7. The method of claim 6, wherein the pair of electrodes is at least partially submerged in the liquid sample.

8. The method of claim 6, wherein applying an electric current comprises applying an alternating current.

9. The method of claim 6, wherein applying an electric current comprises applying a direct current.

10. The method of claim 1, wherein the ion analyzer device is a mass spectrometer or ion mobility spectrometer.

* * * * *